US010722858B2

(12) United States Patent
Fan et al.

(10) Patent No.: US 10,722,858 B2
(45) Date of Patent: *Jul. 28, 2020

(54) METHODS AND COMPOSITIONS FOR TAGGING AND ANALYZING SAMPLES

(71) Applicant: Lineage Biosciences, Inc., Vancouver (CA)

(72) Inventors: Hei-Mun Christina Fan, Fremont, CA (US); Edward A. Hutchins, Mountain View, CA (US)

(73) Assignee: Lineage Biosciences, Inc., Vancouver (CA)

( * ) Notice: Subject to any disclaimer, the term of this patent is extended or adjusted under 35 U.S.C. 154(b) by 191 days.

This patent is subject to a terminal disclaimer.

(21) Appl. No.: 16/043,060

(22) Filed: Jul. 23, 2018

(65) Prior Publication Data

US 2018/0326389 A1 Nov. 15, 2018

Related U.S. Application Data

(63) Continuation of application No. 14/776,177, filed as application No. PCT/US2014/029393 on Mar. 14, 2014, now Pat. No. 10,058,839.

(60) Provisional application No. 61/806,143, filed on Mar. 28, 2013, provisional application No. 61/801,785, filed on Mar. 15, 2013.

(51) Int. Cl.
| *C12Q 1/68* | (2018.01) |
| *B01J 19/00* | (2006.01) |
| *C12N 15/10* | (2006.01) |
| *C12Q 1/6874* | (2018.01) |
| *C12Q 1/6881* | (2018.01) |

(52) U.S. Cl.
CPC ...... B01J 19/0046 (2013.01); C12N 15/1096 (2013.01); C12Q 1/6874 (2013.01); C12Q 1/6881 (2013.01); *B01J 2219/00596* (2013.01); *B01J 2219/00722* (2013.01); *C12Q 2600/16* (2013.01)

(58) Field of Classification Search
CPC .......... B01J 19/0046; B01J 2219/00596; B01J 2219/00722; C12N 15/1096; C12Q 1/6874; C12Q 1/6881; C12Q 2600/16
See application file for complete search history.

(56) References Cited

U.S. PATENT DOCUMENTS

| 4,466,467 A | 8/1984 | Tolliver |
| 5,018,067 A | 5/1991 | Mohlenbrock et al. |
| 5,432,054 A | 7/1995 | Sanders et al. |
| 5,733,729 A | 3/1998 | Lipshutz et al. |
| 5,858,412 A | 1/1999 | Staniforth et al. |
| 5,994,076 A | 11/1999 | Chenchil et al. |
| 6,258,540 B1 | 7/2001 | Lo et al. |
| 6,355,431 B1 | 3/2002 | Chee et al. |
| 6,396,995 B1 | 5/2002 | Stuelpnagel et al. |
| 6,429,027 B1 | 8/2002 | Chee et al. |
| 6,492,144 B1 | 12/2002 | Umansky et al. |
| 6,505,125 B1 | 1/2003 | Ho |
| 6,544,732 B1 | 4/2003 | Chee et al. |
| 6,620,584 B1 | 9/2003 | Chee et al. |
| 6,663,832 B2 | 12/2003 | Lebl et al. |
| 6,770,441 B2 | 8/2004 | Dickinson |
| 6,787,308 B2 | 9/2004 | Balasubramanian et al. |
| 6,812,005 B2 | 11/2004 | Fan et al. |
| 6,833,246 B2 | 12/2004 | Balasubramanian et al. |
| 6,846,460 B1 | 1/2005 | Lebl |
| 6,858,394 B1 | 2/2005 | Chee et al. |
| 6,890,741 B2 | 5/2005 | Fan et al. |
| 6,890,764 B2 | 5/2005 | Chee et al. |
| 6,897,023 B2 | 5/2005 | Fu et al. |
| 6,913,884 B2 | 7/2005 | Stuelpnagel et al. |
| 6,942,968 B1 | 9/2005 | Dickinson et al. |
| 6,969,488 B2 | 11/2005 | Bridgham et al. |
| 6,998,274 B2 | 2/2006 | Chee et al. |
| 7,025,935 B2 | 4/2006 | Jones et al. |
| 7,033,754 B2 | 4/2006 | Chee |
| 7,035,740 B2 | 4/2006 | Kermani |
| 7,040,959 B1 | 5/2006 | Panuska et al. |
| RE39,920 E | 11/2007 | Umansky et al. |
| 7,316,897 B2 | 1/2008 | Bisconte De et al. |
| 7,473,767 B2 | 1/2009 | Dimitrov |
| 7,745,132 B1 | 6/2010 | Rush |
| 7,785,783 B2 | 8/2010 | Morley et al. |
| 7,829,285 B2 | 11/2010 | Lo et al. |
| 8,236,503 B2 | 8/2012 | Faham et al. |
| 8,507,205 B2 | 8/2013 | Faham et al. |
| 8,628,927 B2 | 1/2014 | Faham et al. |
| 8,691,510 B2 | 4/2014 | Faham et al. |
| 8,703,652 B2 | 4/2014 | Quake et al. |

(Continued)

FOREIGN PATENT DOCUMENTS

| CN | 105189748 | 12/2015 |
| CN | 105189749 | 12/2015 |

(Continued)

OTHER PUBLICATIONS

Bolotin et al., "Next Generation Sequencing for TCR Repertoire Profiling: Platform-Specific Features and Correction Algorithms," European Journal of Immunology, vol. 42, pp. 3073-3083, (2012).
Kivioja et al., "Counting Absolute Numbers of Molecules using Unique Molecular Identifiers," Nature Methods, vol. 9(1), pp. 72-74, (2012).
Malomi et al., "Intracellular Expression of P-170 Glycoprotein in Peripheral Blood Mononuclear Cell Subsets from Healthy Donors and HIV-Infected Patients," Haematologica, vol. 83, pp. 13-20, (1998).
Jones et al., "The Taming of a Transposon: V(D) Recombination and the Immune System," Immunological Review, vol. 200, pp. 233-248, (Aug. 2004).
Maizels, "Immunoglobulin Gene Diversification," Annual Reviews of Genetics, vol. 39, pp. 23-46, (Dec. 2005).

(Continued)

*Primary Examiner* — Cynthia B Wilder
(74) *Attorney, Agent, or Firm* — Snell & Wilmer, L.L.P.

(57) ABSTRACT

The invention relates to methods of tagging analytes in a sample.

28 Claims, 18 Drawing Sheets

Specification includes a Sequence Listing.

(56) References Cited

U.S. PATENT DOCUMENTS

| | | |
|---|---|---|
| 8,748,103 B2 | 6/2014 | Faham et al. |
| 8,795,970 B2 | 8/2014 | Faham et al. |
| 10,058,839 B2 | 8/2018 | Fan et al. |
| 2002/0012930 A1 | 1/2002 | Rothberg et al. |
| 2002/0038227 A1 | 3/2002 | Fey et al. |
| 2002/0177141 A1 | 11/2002 | Chee et al. |
| 2002/0187515 A1 | 12/2002 | Chee et al. |
| 2003/0003490 A1 | 1/2003 | Fan et al. |
| 2003/0022207 A1 | 1/2003 | Balasubramanian et al. |
| 2003/0044781 A1 | 3/2003 | Korlach et al. |
| 2003/0058629 A1 | 3/2003 | Hirai et al. |
| 2003/0064398 A1 | 4/2003 | Barnes et al. |
| 2003/0100102 A1 | 5/2003 | Rothberg et al. |
| 2003/0124586 A1 | 7/2003 | Griffiths |
| 2003/0148344 A1 | 8/2003 | Rothberg et al. |
| 2003/0175773 A1 | 9/2003 | Chee et al. |
| 2003/0198573 A1 | 10/2003 | Forood et al. |
| 2004/0106130 A1 | 6/2004 | Besemer et al. |
| 2004/0122296 A1 | 6/2004 | Hatlestad et al. |
| 2004/0122297 A1 | 6/2004 | Stahmann et al. |
| 2004/0137470 A1 | 7/2004 | Dhallan |
| 2004/0185482 A1 | 9/2004 | Stuelpnagel et al. |
| 2004/0224353 A1 | 11/2004 | Fan et al. |
| 2004/0241764 A1 | 12/2004 | Galili |
| 2004/0248161 A1 | 12/2004 | Rothberg et al. |
| 2005/0079510 A1 | 4/2005 | Berka et al. |
| 2005/0100932 A1 | 5/2005 | Lapidus et al. |
| 2005/0124022 A1 | 6/2005 | Srinivasan et al. |
| 2005/0164246 A1 | 7/2005 | Fan et al. |
| 2005/0181394 A1 | 8/2005 | Steemers et al. |
| 2005/0216207 A1 | 9/2005 | Kermani |
| 2005/0244870 A1 | 11/2005 | Chee et al. |
| 2005/0266432 A1 | 12/2005 | Oliphant et al. |
| 2005/0282185 A1 | 12/2005 | Lo et al. |
| 2006/0012784 A1 | 1/2006 | Ulmer |
| 2006/0012793 A1 | 1/2006 | Harris |
| 2006/0019258 A1 | 1/2006 | Yeakley |
| 2006/0024678 A1 | 2/2006 | Buzby |
| 2006/0024711 A1 | 2/2006 | Lapidus et al. |
| 2006/0046258 A1 | 3/2006 | Lapidus et al. |
| 2006/0049274 A1 | 3/2006 | Hume et al. |
| 2006/0078909 A1 | 4/2006 | Srinivasan et al. |
| 2006/0078937 A1 | 4/2006 | Korlach et al. |
| 2006/0259248 A1 | 11/2006 | Collette et al. |
| 2007/0166708 A1 | 7/2007 | Dimitrov et al. |
| 2007/0161001 A1 | 12/2007 | Leshkowitz |
| 2009/0026082 A1 | 1/2009 | Rothberg et al. |
| 2009/0170102 A1 | 7/2009 | Lo et al. |
| 2009/0221620 A1 | 9/2009 | Luke et al. |
| 2009/0263800 A1 | 10/2009 | Wohlgemuth et al. |
| 2010/0041048 A1 | 2/2010 | Diehl et al. |
| 2010/0151471 A1 | 6/2010 | Faham |
| 2010/0261026 A1 | 10/2010 | Ferree et al. |
| 2010/0305000 A1 | 12/2010 | Mathew et al. |
| 2010/0330035 A1 | 12/2010 | Hildebrandt-eriksen et al. |
| 2011/0166029 A1 | 7/2011 | Margulies et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2012/0009649 A1 | 1/2012 | Dahl et al. |
| 2012/0220494 A1* | 8/2012 | Samuels ............ C12N 15/1075 506/16 |
| 2012/0295810 A1 | 11/2012 | Quake et al. |
| 2012/0316074 A1 | 12/2012 | Saxonov |
| 2013/0065768 A1 | 3/2013 | Zheng et al. |
| 2013/0078633 A1 | 3/2013 | Hutchins et al. |
| 2013/0150252 A1 | 6/2013 | Faham et al. |
| 2013/0196328 A1 | 8/2013 | Pepin et al. |
| 2013/0196861 A1 | 8/2013 | Quake et al. |
| 2013/0202718 A1 | 8/2013 | Pepin et al. |
| 2013/0236895 A1 | 9/2013 | Faham et al. |
| 2013/0324422 A1 | 12/2013 | Faham et al. |
| 2014/0255929 A1 | 9/2014 | Zheng |
| 2014/0255944 A1 | 9/2014 | Carlton et al. |
| 2014/0315725 A1 | 10/2014 | Faham et al. |
| 2015/0133317 A1 | 5/2015 | Robinson |
| 2015/0211070 A1 | 7/2015 | Seligson |
| 2016/0001248 A1 | 1/2016 | Hei-Mun et al. |
| 2016/0040234 A1 | 2/2016 | Hutchins et al. |
| 2016/0122830 A1 | 5/2016 | Stephan et al. |
| 2016/0228841 A2 | 8/2016 | Hei-Mun et al. |
| 2016/0251697 A1 | 9/2016 | Nolan |

FOREIGN PATENT DOCUMENTS

| | | |
|---|---|---|
| DE | 10149786 | 7/2003 |
| DE | 10214395 | 10/2003 |
| DE | 10356837 | 6/2005 |
| DE | 102004009704 | 9/2005 |
| DE | 102004025744 | 12/2005 |
| DE | 102004025745 | 12/2005 |
| DE | 102004025746 | 12/2005 |
| DE | 102004025694 | 2/2006 |
| DE | 102004025695 | 2/2006 |
| DE | 102004025696 | 2/2006 |
| EP | 1369477 | 12/2003 |
| EP | 1544308 | 1/2009 |
| EP | 2405020 | 1/2012 |
| EP | 2364368 | 1/2014 |
| WO | 1997024455 | 7/1997 |
| WO | 1999018231 | 4/1999 |
| WO | 2002061148 | 8/2002 |
| WO | 2002088382 A1 | 11/2002 |
| WO | 2003020968 A2 | 3/2003 |
| WO | 2003031947 A2 | 4/2003 |
| WO | 2003044225 | 5/2003 |
| WO | 2002088382 A3 | 8/2003 |
| WO | 2003020968 A3 | 12/2003 |
| WO | 2003031947 A3 | 12/2003 |
| WO | 2004024953 | 3/2004 |
| WO | 2004069849 | 8/2004 |
| WO | 2005003375 | 1/2005 |
| WO | 2005019452 | 3/2005 |
| WO | 2005044836 A2 | 5/2005 |
| WO | 2005059176 | 6/2005 |
| WO | 2005044836 A3 | 7/2007 |
| WO | 2007149432 | 12/2007 |
| WO | 2008103900 | 8/2008 |
| WO | 2008147879 | 12/2008 |
| WO | 2009025852 A2 | 2/2009 |
| WO | 2009060035 | 5/2009 |
| WO | 2009102470 | 8/2009 |
| WO | 2009137255 | 11/2009 |
| WO | 2009152928 | 12/2009 |
| WO | 2010053587 | 5/2010 |
| WO | 2009148560 | 12/2010 |
| WO | 2011057061 | 5/2011 |
| WO | 2011140433 | 11/2011 |
| WO | 2012083069 | 6/2012 |
| WO | 2012148497 | 11/2012 |
| WO | 2014108850 | 7/2014 |
| WO | 2014144713 | 9/2014 |
| WO | 2014144822 | 4/2015 |

OTHER PUBLICATIONS

Peet, "The Measurement of Species Diversity," Annual Review Ecology Systematics, vol. 5, pp. 285-307, (1974).

Tibshirani et al., "Diagnosis of Multiple Cancer Types by Shrunken Centroids of Gene Expression," PNAS, vol. 99, pp. 6567-6572, (2002).

Tusher et al., "Significance Analysis of Microarrays Applied to the Ionizing Radiation Response," PNAS, vol. 98, pp. 5116-5121, (Apr. 2001).

Winter et al., "Dual Enigma of Somatic Hypermutation of Immunoglobulin Variable Genes: Targeting and Mechanism," Immunology Review, vol. 162, pp. 89-96, (1998).

EP; Extended European Search Report dated Oct. 18, 2018 in International Application No. 18174907.8.

USPTO; Advisory Action dated Sep. 26, 2018 in U.S. Appl. No. 14/776,141.

(56) References Cited

OTHER PUBLICATIONS

Simpson, "ABySS: A Parallel Assembler for Short Read Sequence Data," Genome Research, vol. 19, pp. 1117-1123, (2009).
Scinicariello et al., "Rhesus Macaque Antibody Molecules: Sequences and Heterogeneity of Alpha and Gamma Constant Regions," Immunology, col. 111, pp. 66-74, (2004).
Verpoort et al., "Isotypes Distribution of Anti-Cyclic Citrullinated Peptide Antibodies in Undifferentiated Arthritis and Rheumatoid Arthritis Reflects an Ongoing Immune Response," Arthritis and Theumatism, vol. 54, No. 12, pp. 3799-3808, (2006).
Wagner et al., "The Complete Map of the Ig Heavy Chain Constant Gene Region Reveals Evidence for Seven IgG Isotypes and for IgG in the Horse," The Journal of Immunology, vol. 173, pp. 3230-3242, (2004).
Abu-Hamar, et al., "Clinicopatliological Significance and Prognostic Importance of Circulating Plasma DNA Expression in Advanced Non-Small Cell Lung Cancer and Its Efficacy as a Diagnostic Tool," Life Science Journal, vol. 8, pp. 143-150, (p. 147, Table 3), abstract, (Jan. 1, 2011).
Adams, et al., "The Genome Sequence of *Drosophila melanogaster*," Science, vol. 287(5461), pp. 2185-2195, (Mar. 24, 2000).
Agostini et al., "Circulating Cell-Free DNA: A Promising Marker of Pathologic Tumor Response in Rectal Cancer Patients Receiving Preoperative Chemoradiotherapy," Ann Surg. Oncology, vol. 18(9), pp. 2461-2468, (Sep. 2011).
Altin et al., "The Role of CD45 and CD-45 Associated Molecules in T Cell Activation," Immunology Cell Biol., vol. 75, No. 5, pp. 430-445, (1997).
Applied Biosystems, "ABI Prism 7000 Sequence Detection System, Assays-on-Demand Gene Expressions Products Protocol," pp. 1-40, (2003).
Arnaout, RA., "Specificity and Overlap in Gene Segment-Defined Antibody," BMC Genomics, vol. 28, No. 6, p. 148, 9 pages total, (Oct. 28, 2005).
Assie G. et al., "SNP Arraysin Heterogeneous Tissue: Highly Accurate Collection of Both Germline and Somatic Genetic Information from Unpaired Single Tumor Samples," The American Journal of Human Genetics, vol. 82, pp. 903-915, (Apr. 2008).
Barnes et al., "Experimental Comparison and Cross-Validation of the Affymetrix and Illumina Gene Expression Analysis Platforms," Nucleic Acids Res., vol. 33(18), pp. 5914-5923, Print 2005, (Oct. 19, 2005).
Baxter-Lowe et al., "Tracking Microchimeric DNA in Plasma to Diagnose and Manage Organ Transplant Rejection," Clin. Chem., vol. 52(4), pp. 559-561, (Apr. 2006).
Beck, J. et al., "Next Generation Sequencing of Serum Circulating Nucleic Acids from Patients with Invasive Ductal Breast Cancer Reveals Differences to Healthy and Nonmalignant Controls," Molecular Cancer Res, vol. 8(3), pp. 335-342, Supplementary Information, (Mar. 2010).
Bettegowda, C. et al., "Detection of Circulating Tumor DNA in Early- and Late-Stage Human Malignancies," Science Transl. Med, vol. 6(224):224ra24, (Feb. 19, 2014).
Bianchi et al., "Isolation of Fetal DNA from Nucleated Erythrocytes in Maternal Blood," Proc Natl Acad Sci USA., vol. 87(9), pp. 3279-3283, (May 1990).
Bibikova et al., "Gene Expression Profiles in Formalin-Fixed, Paraffin-Embedded Tissues Obtained with a Novel Assay for Microarray Analysis," Clinical Chem., vol. 50(12), pp. 2384-2386, (Dec. 2004).
Borrill et al., "The Use of Short Tandem Repeat Polymorphisms for Monitoring Chimerism Following Bone Marrow Transplantation: A Short Report," Hematology, vol. 13(4), pp. 210-214, (Aug. 2008).
Bossola et al., "Circulating Bacterial-Derived DNA Fragments and Markers of Inflammation in Chronic Bemodialysis Patients," Clinical J Am Soc. Nephrol., vol. 4(2), pp. 379-385, (Feb. 2009).
Boyd et al., "Measurement and Clinical Monitoring of Human Lymphocyte Clonality by Massively Parallel VDJ Pyrosequencing," Sci. Transl. Med., vol. 1(12), p. 12-23 (16 pages), (Dec. 23, 2009).

Bruch et al., "Tropboblast-Like Cells Sorted from Peripheral Maternal Blood using Flow Cytometry: A Multiparametric Study Involving Transmission Electron Microscopy and Fetal DNA Amplification," Prenatal Diagnosis, vol. 11(10), pp. 787-798, (Oct. 11, 1991).
Cai et al., "Assessing Self-Renewal and Differentiation in Human Embryonic Stem Cell Lines," Stem Cells, vol. 24(3), pp. 516-530. (Mar. 2006).
Campbell, "Subclonal Phylogenetic Structures in Cancer Revealed by Ultra-Deep Sequencing," PNAS, vol. 105 No. 35, pp. 13081-13086, (2008).
Chen et al., "Telomerase RNA as a Detection Marker in the Serum of Breast Cancer Patients," Clinical Cancer Research, vol. 6(10), pp. 3823-3826, (Oct. 2000).
Cheng et al., "Quantification of Circulating Cell-Free DNA in the Plasma of Cancer Patients During Radiation Therapy," Cancer Sci., vol. 100(2), pp. 303-309, (Feb. 2009).
Curran et al., "Nucleotide Sequencing of Psoriatic Arthritis Tissue Before and During Methotrexate Administration Reveals a Complex Inflammatory T Cell Infiltrate with Very Few Clones Exhibiting Features That Suggest They Drive the Inflammatory Process by Recognizing Autoantigens," The Journal of Immunology, vol. 172, No. 3, pp. 1935-1944, (2004).
Damle et al., "B-Cell Chronic Lymphocytic Leukemia Cells Express a Surface Membrane Phenotype of Activated, Antigen-Experienced B Lymphocytes," Blood, vol. 99, No. 11, pp. 4087-4093, (2002).
Dawson, S.J.et al., "Analysis of Circulating Tumor DNA to Monitor Metastatic Breast Cancer," New England Journal of Medicine, vol. 368, pp. 1199-1209, (Mar. 28, 2013).
De La Vega et al., "Assessment of Two Flexible and Compatible SNP Genotyping Platforms; TaqMan SNP Genotyping Assays and the SNPlex Genotyping System," Mutat Res., vol. 573(1-2), pp. 111-135, (Jun. 3, 2005).
De Mattos-Arruda, D. and Caldas, C., "Cell-Free Circulating Tumour DNA as a Liquid Biopsy in Breast Cancer," Molecular Oncology, vol. 10, pp. 464-474, (2016).
De Vlaminck et al., "Circulating Cell-Free DNA Enables Noninvasive Diagnosis of Heart Transplant Rejection," Science Transl. Med., vol. 6(241), (Jun. 18, 2014).
De Vlaminck, et al., "Supplementary Materials for Circulating Cell-Free DNA Enables Noninvasive Diagnosis of Heart Transplant Rejection," Science Transl. Med., vol. 6(241), (Jun. 18, 2014).
Demirci et al., "Direct Etch Method for Microfludic Channel and Nanoheight Postfabrication by Picoliter Droplets," Applied Physics Letters, vol. 88(5), pp. 053117-053117-3, (Jan. 2006).
Di et al., "Dynamic Model Based Algorithms for Screening and Genotyping Over 100 K SNPs on Oligonucleotide Microarrays," Bioinformatics, vol. 21(9), pp. 1958-1963, (May 1, 2005).
Diehl et al., "Circulating Mutant DNA to Assess Tumor Dynamics," Nat Med., vol. 14(9), pp. 985-990, (Sep. 2008).
Diehl et al., "Detection and Quantification of Mutations in the Plasma of Patients with Colorectal Tumors," Proc Natl Acad. Sci. USA, vol. 102(45), pp. 16368-73,(Nov. 8, 2005).
Diluvio et al., "Identical TCR Beta-Chain Rearrangements in Streptococcal Angina and Skin Lesions of Patients with Psoriasis Vulgaris," J. Immunology, vol. 176, No. 11, pp. 7104-7111, (2006).
Dressman et al., "Transforming Single DNA Molecules into Fluorescent Magnetic Particles for Detection and Enumeration of Genetic Variations," PNAS, vol. 100. No. 15, pp. 8817-8822, (2003).
Faham et al., "Mismatch Repair Detection (MRD): High-Throughput Scanning for DNA Variations," Hum Molecular Genet, vol. 10(16), pp. 1657-1664, (Aug. 1, 2001).
Fakhrai-Rad et al., "SNP Discovery in Pooled Samples with Mismatch Repair Detection," Genome Res., vol. 14(7), pp. 1404-1412, (Jul. 2004).
Fan et al., "Detection of Aneuploidy with Digital Polymerase Chain Reaction," Anal Chem., vol. 79(19), pp. 7576-7579, (Oct. 1, 2007).
Fan et al., "Noninvasive Diagnosis of Fetal Aneuploidy by Shotgun Sequencing DNA from Maternal Blood," Proc Natl Acad Sci USA, vol. 105(42), pp. 16266-16271, (Oct. 21, 2008).
Fitzgerald et al., "Intravascular Ultrasound Imaging of Coronary Arteries. Is Three Layers the Norm?" Circulation, vol. 86(1), pp. 154-158, (Jul. 1992).

(56) References Cited

OTHER PUBLICATIONS

Fiegl H. et al., "Circulating Tumor-Specific DNA: A Marker for Monitoring Efficacy of Adjuvant Therapy in Cancer Patients," Cancer Res 2005, vol. 65(4), pp. 1141-1145, (Feb. 15, 2005).
Fournie et al., "Plasma DNA as a Marker of Cancerous Cell Death. Investigations in Patients Suffering from Lung Cancer and in Nude Mice Bearing Human Tumours," Cancer Lett, vol. 91(2), pp. 221-227, (May 8, 1995).
Freeman et al., "Profiling the T-Cell Receptor Beta-Chain Repertoire by Massively Parallel Sequencing," Genome Research, vol. 19, pp. 1817-1824, (2009).
Furmanski et al., "Public T Cell Receptor Beta-Chains are not Advantaged during Positive Selection," J lmmunol, vol. 180, pp. 1029-1039, (Jan. 2008).
Gadi et al., "Soluble Donor DNA Concentrations in Recipient Serum Correlate with Pancreas-Kidney Rejection," Clin Chem., vol. 52(3), pp. 379-382, (Mar. 2006).
Garcia-Moreira et al., "Cell-Free DNA as a Noninvasive Acute Rejection Marker in Renal Transplantation," Clin Chem., vol. 55(11), pp. 1958-1966, (Nov. 2009).
Giacona et al., "Cell-Free DNA in Human Blood Plasma: Length Measurements in Patients with Pancreatic Cancer and Healthy Controls," Pancreas, vol. 17(1), pp. 89-97, (Jul. 1998).
Glanville et al., "Precise Determination of the Diversity of a Combinatorial Antibody Library Gives Insight into the Human Immunoglobulin Repertoire," PNAS, vol. 106, No. 48, pp. 20216-20221, (Dec. 1, 2009).
Gonzalez et al., "Multiple Displacement Amplification as a Pre-Polymerase Chain Reaction (pre-PCR) to Process Difficult to Amplify Samples and Low Copy Number Sequences from Natural Environments," Environ Microbiology, vol. 7(7), pp. 1024-1028, (Jul. 2005).
Han et al., "lmmunorepertoire Analysis by Multiplex PCR Amplification and High Throughput Sequencing," (Abstract) J. lmmunol., p. 182, (Meeting Abstract Supplement) 42.6., (2009).
Hardenbol et al., "Highly Multiplexed Molecular Inversion Probe Genotyping: Over 10,000 Targeted SNPs Genotyped in a Single Tube Assay," Genome Res., vol. 15(2), pp. 269-275, (Feb. 2005).
Hardenbol et al., "Multiplexed Genotyping with Sequence-Tagged Molecular Inversion Probes," Nat Biotechnol., vol. 21(6), pp. 673-678, (Jun. 2003).
Hermanson, "Bioconjugate Techniques," Academic Press, San Diego, CA. 1996. Journal of Medicinal Chemistry (Impact Factor; 5.48), vol. 40(4), pp. 631, (Feb. 1997).
Herzenberg et al., "Fetal Cells in the Blood of Pregnant Women: Detection and Enrichment by Fluorescence-Activated Cell Sorting," Proc Natl Acad Sci USA, vol. 76(3), pp. 1453-1455, (Mar. 1979).
Hubacek et al., "Detection of Donor DNA After Heart Transplantation. How Far Could it be Affected by Blood Transfusion and Donor Chimerism?" Transplant Proc., vol. 39(5), pp. 1593-1595, (Jun. 2007).
Huber et al., "High-Resolution Liquid Chromatography of DNA Fragments on Non-Porous Poly(Styrene-Divinylbenzene) Particles," Nucleic Acids Research, vol. 21(5), pp. 1061-1066, (Mar. 1993).
Irimia et al., "Universal Microfluidic Gradient Generator," Analytical Chemistry, vol. 78, pp. 3472-3477, (2006).
Kacharmina et al., "Preparation of cDNA from Single Cells and Subcellular Regions," Methods Enzymol, vol. 303, pp. 3-18, (1999).
Kato et al., "A New Packing for Separation of DNA Restriction Fragments by High Performance Liquid Chromatography," J. Biochem., vol. 95(1), pp. 83-86, (Jan. 1984).
Kita et al., "T Cell Receptor Clonotypes in Skin Lesions from Patients with Systemic Lupus Erythematosus," The Journal of Investigative Dermatology, vol. 110, pp. 41-46, (1998).
Kobashigawa et al., "Multicenter Intravascular Ultrasound Validation Study Among Heart Transplant Recipients: Outcomes After Five Years," J, American College of Cardiology, vol. 45(9), pp. 1532-1537, (May 3, 2005).
Kounalakis et al., "Tumor Cell and Circulating Markers in Melanoma: Diagnosis Prognosis, and Management," Current Oncology Reports, vol. 7(5), pp. 377-382, (Sep. 2005).
Leary R.J. et al., "Development of Personalized Tumor Biomarkers Using Massively Parallel Sequencing," Science Translational Medicine, vol. 2, Issue 20, pp. 1-7, (Feb. 24, 2010).
Levene et al., "Zero-Mode Waveguides for Single-Molecule Analysis at High Concentrations," Science, vol. 299(5607), pp. 682-686, (Jan. 31, 2003).
Leykin et al., "Comparative Linkage Analysis and Visualization of High-Density Oligonucleotide SNP Array Data," BMC Genet, vol. 6(7), pp. 1-16, (Feb. 15, 2005).
Liu et al., "Algorithms for Large-Scale Genotyping Microarrays," Bioinformatics, vol. 19(18), pp. 2397-2403, (Dec. 12, 2003).
Livak et al., "Towards Fully Automated Genome-Wide Polymorphism Screening," Nature Genetics, vol. 9, pp. 341-342, (1995).
Lo et al., "Molecular Testing of Urine: Catching DNA on the Way Out," Clinical Chemistry, vol. 46(8 Pt 1), pp. 1039-1040, (Aug. 2000).
Lo et al., "Plasma Nucleic Acid Analysis by Massively Parallel Sequencing: Pathological Insights and Diagnostic Implications," J. Pathol, vol. 225, pp. 318-323, (2011).
Lo et al., "Presence of Donor-Specific DNA in Plasma of Kidney and Liver-Transplant Recipients," Lancet, vol. 351(9112), pp. 1329-1330, (May 2, 1998).
Lo et al., "Quantitative Analysis of Fetal DNA in Maternal Plasma and Serum: Implications for Noninvasive Prenatal Diagnosis," Am J Hum Genet, vol. 62(4), pp. 768-775, (Apr. 1998).
Lo, "Transplantation Monitoring by Plasmas DNA Sequencing," Clinical Chemistry, vol. 57(7), pp. 941-942, (Jul. 2011).
Lui et al., "Origin of Plasma Cell-Free DNA After Solid Organ Transplantation," Clinical Chemistry, vol. 49(3), pp. 495-496, (Mar. 2003).
Maheswaran et al., "Detection of Mutations in EGFR in Circulating Lung-Cancer Cells," New England Journal of Medicine, vol. 359(4), pp. 366-377, (Jul. 24, 2008).
Mandel et al., "Nucleic Acids of the Blood Plasma in Humans," CR Seances Soc Biol Fil., vol. 142(3-4), pp. 241-243, (Feb. 1948).
Mardis, "Next-Generation DNA Sequencing Methods," Annu Rev. Genomics Hum. Genet, vol. 9, pp. 387-402, (Sep. 2008).
Miceli et al., "The Roles of CD4 and CD8 in T Cell Activation," Semin. lmmunol, vol. 3, No. 3., pp. 133-141, abstract only, (1991).
Murray, "Evaluation of Linkage Disequilibrium and its Effect on Non-Parametric Multipoint Linkage Analysis using Two High Density Single-Nucleotide Polymorphism Mapping Panels," BMC Genetics, vol. 6 Supplemental 1, p. S85, (Dec. 30, 2005).
Ng et al., "mRNA of Placental Origin is Readily Detectable in Maternal Plasma," Proc Natl Acad Sci USA, vol. 100(8), pp. 4748-4753, (Apr. 15, 2003).
Ng et al., "The Concentration of Circulating Corticotropin-Releasing Hormone mRNA in Maternal Plasma is Increased in Preeclampsia." Clin Chem., vol. 49(5), pp. 727-731, (May 2003).
O'Driscoll L. et al., "Feasibility and Revelance of Global Expression Profiling of Gene Transcripts in Serum from Breast Cancer Patients Using Whole Genome Microarrays and Quantitative RT-PCR," Cancer Genomics and Proteomics, vol. 5, pp. 95-104, (2008).
Pabon et al., "Optimized T7 Amplification System for Microarray Analysis," Biotechniques, vol. 31(4), pp. 874-879, (Oct. 2001).
Robins et al., "Comprehensive Assessment of T-Cell Receptor 13-Chain Diversity in al3 T Cells," Blood, vol. 114, No. 19, pp. 4099-4107, (Nov. 5, 2009).
Ruschendorf et al. "ALOHOMORA: a tool for linkage analysis using 1OK SNP array data," Bioinformatics, vol. 21(9), pp. 2123-2125, (May 1, 2005).
Sambrook et al., 2nd. Edition, "Molecular Cloning: A Laboratory Manual," (1989).
Schwartz et al., "NTera2: A Model System to Study Dopaminergic Differentiation of Human Embryonic Stem Cells," Stem Cells Dev., vol. 14(5), pp. 517-534, (Oct. 2005).
Schwarzenbach H. et al., "Cell-Free Nucleic Acids as Biomarkers in Cancer Patients," Nature Reviews Cancer. AOP, pp. 1-12, (May 2011).

(56) References Cited

OTHER PUBLICATIONS

Schwarzenbach et al., "Detection and Monitoring of Cell-Free DNA in Blood of Patients with Colorectal Cancer," Ann NY Acad Sci., vol. 1137, pp. 190-196, (Aug. 2008).
Shaw, J.A. et al., "Circulating Free DNA in the Management of Breast Cancer," Ann Transl Med, vol. 2(1), p. 3, (2014).
Shaw, J.A. et al., "Genomic Analysis of Circulating Cell-Free DNA Infers Breast Cancer Dormancy," Genome Res, vol. 22(2), pp. 220-231, (Feb. 2012).
Shen et al., "High-Throughput SNP Genotyping on Universal Bead Arrays," Mutation Research, vol. 573(1-2), pp. 70-82, (Jun. 3, 2005).
Shendure et al., "Next-Generation DNA Sequencing," Nature Biotechnology, vol. 26, pp. 1135-1145, (Oct. 9, 2008).
Shendure et al., "Advanced Sequencing Technologies: Methods and Goals," Nat. Rev. Genet., vol. 5, No. 5, pp. 335-344, (May 2004).
Skulina et al., "Multiple Sclerosis: Brain-Infiltrating CD8+ T Cells Persist as Clonal Expansions in the Cerebrospinal Fluid and Blood," PNAS, vol. 100, No. 8, pp. 2428-2433, (2004).
Stanley, "Chapter 7, T Cells," Essentials of Immunology & Serology, Delman, Thomson Learning, p. 95, (2002).
Stranger et al., "Genome-Wide Associations of Gene Expression Variation in Humans," PLoS Genet., vol. 1(6), p. 695-704, (Dec. 2005).
Striebich et al., "Selective Accumulation of Related CD4+ T Cell Clones in the Synovial Fluid of Patients with Rheumatoid Arthritis," J. Imm vol. 161, pp. 4428-4436, (Oct. 15, 1998).
Synder et al., "Supporting Information: Universal noninvasive detection of solid organ transplant rejection," Proc Natl Acad Sci USA, vol. 108(15), pp. 6229-6234, (Apr. 12, 2011).
Synder, et al., "Universal Noninvasive Detection of Solid Organ Transplant Rejection," Proc Natl Acad Sci USA, vol. 108(15), pp. 6229-6234, (Apr. 12, 2011).
Taylor et al., "Registry of the International Society for Heart and Lung Transplantation Twenty-Fifth Official Adult Heart Transplant Report—2008," J Heart Lung Transplant, vol. 27(9), pp. 943-956, (Sep. 2008).
Thomas R.K. et al., "Sensitive Mutation Detection in Heterogeneous Cancer Specimens by Massively Parallel Picoliter Reactor Sequencing," Nature Medicine, vol. 12(7), pp. 852-855. (Jul. 2006).
Tong et al., "Diagnostic Developments Involving Cell-Free (Circulating) Nucleic Acids," Clin Chim Acta., vol. 363(1-2), pp. 187-196, (Jan. 2006).
Umetani N. et al., "Prediction of Breast Tumor Progression by Integrity of Free Circulating DNA in Serum," Journal of Clinical Oncology, vol. 24, No. 26, pp. 4270-4276, (2006).
Universite de Liege, "Roche 454 FLX Technology: How It Works," located at http://www.giga.ulg.ac.be/jcms/cdu_15721/fr/roche-454-flx-technology-how-it-works, 2 pages, (Oct. 10, 2014).
Van Gelder et al., "Amplified RNA Synthesized from Limited Quantities of Heterogeneous cDNA," Proc Natl Acad Sci USA, vol. 87(5), pp. 1663-1667, (Mar. 1990).
VanderBorght et al., "Dynamic T Cell Receptor Clonotype Changes in Synovial Tissue of Patients with Early Rheumatoid Arthritis: Effects of Treatment with Cyclosporin A (Neoral)," J. Rheumatology, vol. 29, No. 3, pp. 416-426, (2002).
Venter et al., "The Sequence of the Human Genome," Science, vol. 291(5507), pp. 1304-1351, (Feb. 16, 2001).
Vymetalova et al., "High Prevalence of Microchimerism in Female Patients," Transplant Proc., vol. 40(10), pp. 3685-3687, (Dec. 2008).
Wang et al., "HIV Integration Site Selection: Analysis by Massively Parallel Pyrosequencing Reveals Association with Epigenetic Modifications," Genome Res., vol. 17, No. 8, pp. 1186-1194, (2007).
Wang et al., "Immunorepertoire Analysis by Multiplex PCR Amplification and High Throughput Sequencing," (Poster—Program 42.6), The 96th Annual Meeting of the American Association of Immunologists, Seattle, Washington, (May 2009).
Wang et al., "High Throughput Sequencing Reveals a Complex Pattern of Dynamic Interrelationships Among Human T Cell Subsets," PNAS, vol. 107, No. 4, pp. 1518-1523, (Jan. 26, 2010).
Warren et al., "Transcription Factor Profiling in Individual Hematopoietic Progenitors by Digital RT-PCR," Proc Natl Acad Sci USA, vol. 103(47), pp. 17807-17812, (Nov. 21, 2006).
Warren et al., "Profiling Model T-Cell Metagenomes with Short Reads," Bioinformatics, vol. 25, No. 4, pp. 458-464, (2009).
Warren et al., "Exhaustive T-Cell Repertoire Sequencing of Human Peripheral Blood Samples Reveals Signatures of Antigen Selection and a Directly Measured Repertoire Size of at Least 1 Million Clonotypes," Genome Research, vol. 27, pp. 790-797, (2011).
Weinstein et al., "High-Throughput Sequencing of the Zebrafish Antibody Repertoire," Science, vol. 324, pp. 807-810, (May 8, 2009).
Heyer et al., "Exploring Expression Data: Identification and Analysis of Coexpressed Genes," Genome Res., vol. 9, pp. 1106-1115, (1999).
Cameron et al. "Expression of IL-4, CE RNA, and IE RNA in the Nasal Mucosa of Patients With Seasonal Rhinitis: Effect of Topical Corticosteroids." J. Allergy Clin. Lmmunol, vol. 101(3), pp. 330-336, (1998).
Cheung et al. "A Recombinant Human Fab Expressed in *Escherichia coli* Neutralizes Rabies Virus." J. Viral., vol. 66(11), pp. 6714-6720, (1992).
Cook. "Use and Misuse of the Receiver Operating Characteristic Curve in Risk Prediction." Circulation, vol. 115, pp. 928-935, (2007).
Harris et al. "Single-Molecule DNA Sequencing of a Viral Genome." Science, vol. 320, pp. 106-109, (2008).
Margulies et al. "Genome Sequencing in Microfabricated High-Density Picolitre Reactors," Nature, vol. 437, pp. 376-380, (2005).
Moudrianakis et al. "Base Sequence Determination in Nucleic Acids with the Electron Microscope, Ill." PNAS, vol. 53, pp. 564-571, (1965).
O'Marcaigh et al. "Estimating the Predictive Value of a Diagnostic Test, How to Prevent Misleading or Confusing Results," Clin. Ped, vol. 32(8), pp. 485-491, (1993).
Pepe et al. "Limitations of the Odds Ratio in Gauging the Performance of a Diagnostic, Prognostic, or Screening Marker," Am. J. Epidemiol. vol. 159(9), pp. 882-890, (2004).
Shultz. "Clinical Interpretation of Laboratory Procedures," Teitz Fundamentals of Clinical Chemistry. Burtis et al., eds. Philadelphia: W. B. Saunders & Co., pp. 192-199, (1996).
Soni et al. "Progress Toward Ultrafast DNA Sequencing Using Solid-State Nanopores." Clin. Chem., vol. 53.11, pp. 1996-2001, (2007).
Tie et al., "Circulating Tumor DNA as an Early Marker of Therapeutic Response in Patients with Metastatic Colorectal Cancer," Annals of Oncology, vol. 26(8), pp. 1715-1722, (Aug. 2015).
Wang et al. "A Custom 148 Gene-Based Resequencing Chip and the SNP Explorer Software: New Tools to Study Antibody Deficiency," Hum. Mutat, vol. 31(9), pp. 1080-1088, (2010).
Weckert et al. "Quantifiable Analysis of Human Immunoglobulin in Heavy Chain Class-Switch Recombination to All Isotypes," J. lmmunol. Meth, vol. 233.1-2, pp. 141-158, (2000).
White. "Restriction-PCR Fingerprinting of the Immunoglobulin VH Repertoire: Direct Detection of an Immune Response and Global Analysis of B Cell Clonality," Eur. J. lmmunol, vol. 28(10), pp. 3268-3279, (1998).
Williams "Rheumatoid Factor Isotype Switch and Somatic Mutation Variants Within Rheumatoid Arthritis Synovium." lmmunol, vol. 98, pp. 123-136, (1999).
Zweig et al. "ROC Curve Analysis: An Example Showing the Relationships Among Serum Lipid and Apolipoprotein Concentrations in Identifying Subjects With Coronary Artery Disease." Clin. Chem., vol. 38(8), pp. 1425-1428, (1992).
Hug et al., "Measurement of the Number of Molecules of a Single mRNA Species in a Complex mRNA Preparation," J. Theor. Biol., vol. 221, No. 4, pp. 615-624, (Apr. 1, 2003).
Georgiou, et al., "The Promise and Challenge of High-Throughput Sequencing of the Antibody Repertoire," Nature Biotechnology, vol. 32, No. 2, pp. 158-168, (Feb. 2, 2014).

(56) References Cited

OTHER PUBLICATIONS

Jiang Ning, et al., "Lineage Structure of the Human Antibody Repertoire in Response to Influenza Vaccination", Science Translational Medicine, vol. 5(171), pp. 171-174, (Feb. 6, 2013).
Schramm, et al., "A Simple and Reliable 5'-Race Approach," Nucleic Acids Research. Oxford University Press. GB, vol. 28(22), pp. 1-4, (Nov. 15, 2000).
Wang, et al., "High-Fidelity mRNA Amplification for Gene Profiling," Nature Biotechnology. Nature Publishing Group. New York. NY. US, vol. 18, pp. 457-459, (Apr. 1, 2000).
Kelly et al., "Miniaturizing Chemistry and Biology in Microdroplets," The Royal Society of Chemistry, pp. 1773-1788, (Feb. 23, 2007).
Hashimshony, et al., "CEL-Seq: Single-Cell RNA-Seq by Multiplexed Linear Amplification," Cell Rep., vol. 2, No. 3, pp. 666-673, (Sep. 1, 2012).
Islam, et al., "Characterization of the Single-Cell Transcriptional Landscape by Highly Multiplex RNA-Seq," Genome Res., vol. 21, No. 7, pp. 1160-1167, (Jul. 2011).
Nakato, et al., "Single-Molecule Reverse Transcription Polymerase Chain Reaction Using Water-In-Oil Emulsion," J Biosci Bioeng, vol. 99, No. 3, pp. 293-295, (Mar. 1, 2005).
Zhang et al., "Presence of Donor- and Recipient-Derived DNA in Cell-Free Urine Samples of Renal Transplantation Recipients: Urinary DNA Chimerism," Clinical Chemistry, vol. 45(10), pp. 1741-1746, (Oct. 1999).
Zheng et al., "Nonhematopoietically Derived DNA is Shorter than Hematopoietically Derived DNA in Plasma: A Transplantation Model," Clinical Chemistry, vol. 58(3), pp. 549-558, (Mar. 2012).
Zhong et al., "Cell-Free DNA in Urine: A Marker for Kidney Graft Rejection, But Not for Prenatal Diagnosis?" Annals NY Academy of Science, vol. 945, pp. 250-257, (Sep. 2001).
EP; European Search Report dated Mar. 26, 2015 in International Application No. 12834150.0.
PCT; International Search Report and Written Opinion dated Jan. 26, 2011 in International Application No. PCT/US2010/055604.
PCT; International Search Report and Written Opinion dated Jan. 7, 2013 in International Application No. PCT/US2012/056416.
PCT; International Preliminary Search Report on Patentability dated Apr. 3, 2014 in International Application No. PCT/US2012/056416.
PCT; International Search Report and Written Opinion dated Dec. 22, 2014 in International Application No. PCT/US2014/029393.
PCT; International Search Report and Written Opinion dated Oct. 10, 2014 in International Application No. PCT/US2014/029241.
USPTO; Office Action dated May 10, 2013 for U.S. Appl. No. 13/508,318.
USPTO; Final Office Action dated Nov. 14, 2013 for U.S. Appl. No. 13/508,318.
USPTO; Notice of Allowance dated Feb. 12, 2014 for U.S. Appl. No. 13/508,318.
USPTO; Non-Final Office Action dated Jun. 9, 2014 in U.S. Appl. No. 13/625,645.
USPTO; Final Office Action dated Feb. 18, 2015 in U.S. Appl. No. 13/625,645.
USPTO; Requirement for Restriction dated Jul. 15, 2015 in U.S. Appl. No. 14/346,293.
USPTO; Non-Final Office Action dated Feb. 2, 2016 in U.S. Appl. No. 14/346,293.
USPTO; Non-Final Office Action dated Mar. 30, 2016 in U.S. Appl. No. 13/625,645.
USPTO; Final Office Action dated Oct. 18, 2016 in U.S. Appl. No. 14/346,293.
USPTO; Non-Final Office Action dated Jun. 27, 2017 in U.S. Appl. No. 13/625,645.
USPTO; Requirement for Restriction dated Jul. 28, 2017 in U.S. Appl. No. 14/776,177.
USPTO; Non-Final Office Action dated Oct. 30, 2017 in U.S. Appl. No. 14/776,177.
USPTO; Non-Final Office Action dated Nov. 2, 2017 in U.S. Appl. No. 14/776,141.
USPTO; Non-Final Office Action dated Nov. 2, 2017 in U.S. Appl. No. 14/346,293.
USPTO; Notice of Allowance dated Apr. 23, 2018 in U.S. Appl. No. 14/776,177.
USPTO; Final Office Action dated Apr. 27, 2018 in U.S. Appl. No. 14/346,293.
USPTO; Notice of Allowance dated May 3, 2018 in U.S. Appl. No. 14/776,177.
USPTO; Final Office Action dated Jun. 21, 2018 in U.S. Appl. No. 14/776,141.

* cited by examiner

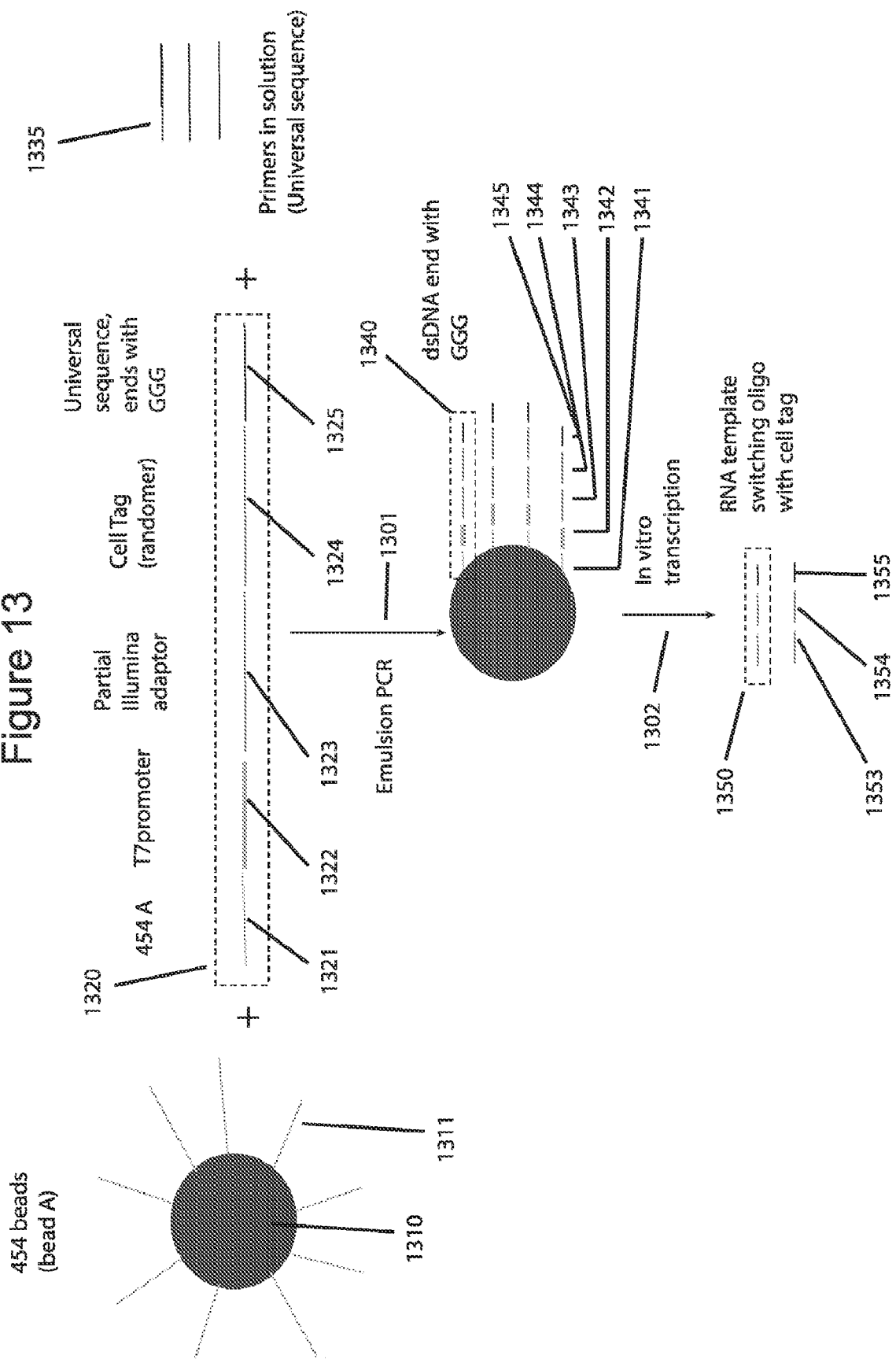

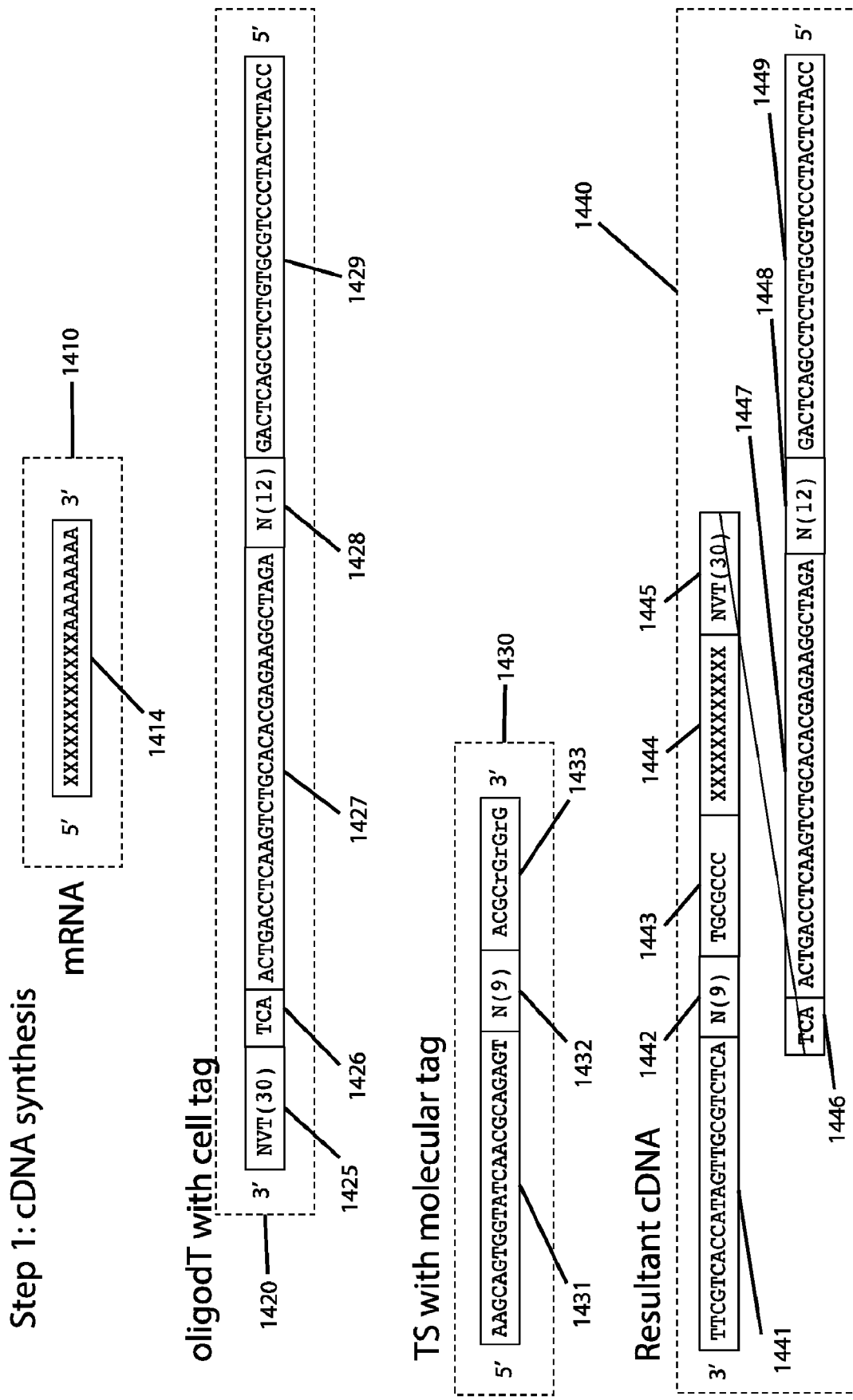

Figure 15

Step 2: Pool cDNA from all cells and Conduct Universal PCR

Resultant cDNA

3' TTCGTCACCATAGTTGCGTCTCA | N(9) | TGCGCCC | XXXXXXXXXX | NVT(30)
TCA | ACTGACCTCAAGTCTGCACACGAGAAGGCTAGA | N(12) | GACTCAGCCTCTGTGCGTCCCTACTCTACC 5'

Step 3: Melt PCR products and Circularize ssDNA

3' ACTGACCTCAAGTCTGCACACGAGAAGGCTAGA | N(12) | GACTCAGCCTCTGTGCGTCCCTACTCTACC

TTCGTCACCATAGTTGCGTCTCA | N(9) | TGCGCCC | XXXXXXXXXX | NVT(30) | TCA 5'

Step 4: Target specific PCR (panel of genes of interest e.g. heavy, light chain)

3' ACTGACCTCAAGTCTGCACACGAGAAGGCTAGA | N(12) | GACTCAGCCTCTGTGCGTCCCTACTCTACC

TTCGTCACCATAGTTGCGTCTCA | N(9) | TGCGCCC | XXXXXXXXXX 5'

Step 5: Sequencing (both cell and molecular tags are read)

Figure 16

Option 1 (bead mode):

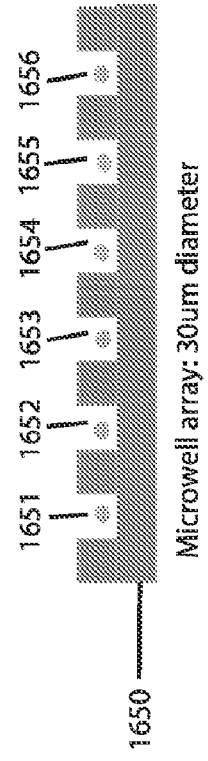

1611 1612 1613 1614 1615 1616 — 1610

Microwell array: 100um diameter
Beads coupled with oligodT with different tag deposited by gravity, submerged in cDNA master mix with random TS oligo 1621 1622 1623 1624 1625 1626 — 1620

Microwell array: 30um diameter
Cells in PBS deposited by gravity

1601 ——— Align microwell arrays

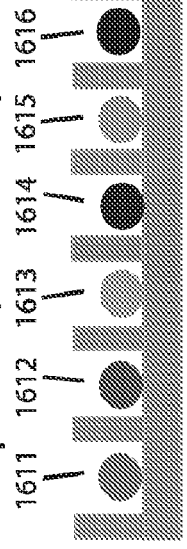

1631 1632 1633 1634 1635 1636 — 1630

Cells lyse when in contact with cDNA mix
42C incubator
Collect beads
Universal PCR with beads

1602

Option 2 (microarray mode):

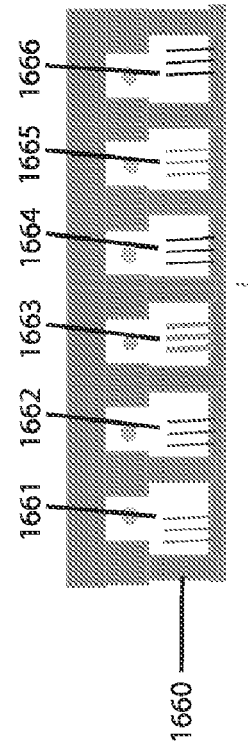

1641 1642 1643 1644 1645 1646

Align ~100um thick PDMS membrane on to glass
Add cDNA mix into wells

1640

1651 1652 1653 1654 1655 1656

Microwell array: 30um diameter
Cells in PBS deposited by gravity

1650

Align microarray and microwell array ——— 1603

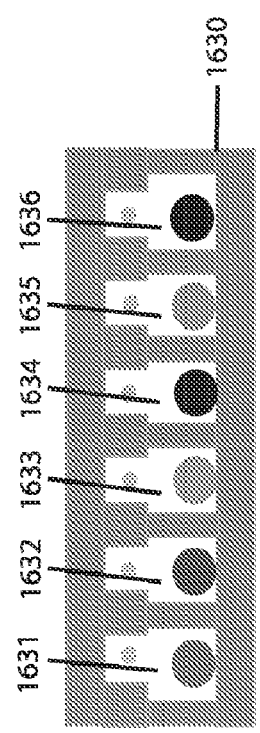

1661 1662 1663 1664 1665 1666

Cells lyse when in contact with cDNA mix
42C incubator
Remove microwell array and membrane
PCR on slide

| randomer length | possible combinations |
|---|---|
| 9 | 2.62E+05 |
| 10 | 1.05E+06 |
| 11 | 4.19E+06 |
| 12 | 1.68E+07 |
| 13 | 6.71E+07 |
| 14 | 2.68E+08 |

SEQUENCE LISTING

<160> NUMBER OF SEQ ID NOS: 20

<210> SEQ ID NO 1
<211> LENGTH: 16
<212> TYPE: DNA
<213> ORGANISM: Artificial Sequence
<220> FEATURE:
<223> OTHER INFORMATION: synthetic oligonucleotide tag
<220> FEATURE:
<221> NAME/KEY: misc_feature
<222> LOCATION: (1)..(9)
<223> OTHER INFORMATION: n is a, c, g, t or u
<220> FEATURE:
<221> NAME/KEY: misc_feature
<222> LOCATION: (14)..(16)
<223> OTHER INFORMATION: may be ribonucleotides

<400> SEQUENCE: 1
nnnnnnnnna cgcggg                                                       16

<210> SEQ ID NO 2
<211> LENGTH: 16
<212> TYPE: DNA
<213> ORGANISM: Artificial Sequence
<220> FEATURE:
<223> OTHER INFORMATION: synthetic oligonucleotide tag
<220> FEATURE:
<221> NAME/KEY: misc_feature
<222> LOCATION: (8)..(16)
<223> OTHER INFORMATION: n is a, c, g, or t

<400> SEQUENCE: 2
cccgcgtnnn nnnnnn                                                       16

<210> SEQ ID NO 3
<211> LENGTH: 20
<212> TYPE: DNA
<213> ORGANISM: Artificial Sequence
<220> FEATURE:
<223> OTHER INFORMATION: synthetic polyA tail sequence
<220> FEATURE:
<221> NAME/KEY: misc_feature
<222> LOCATION: (1)..(12)
<223> OTHER INFORMATION: n is a, c, g, or t

<400> SEQUENCE: 3
nnnnnnnnnn nnaaaaaaaa                                                   20

<210> SEQ ID NO 4
<211> LENGTH: 30
<212> TYPE: DNA
<213> ORGANISM: Artificial Sequence
<220> FEATURE:
<223> OTHER INFORMATION: NVT region synthetic oligonucleotide
<220> FEATURE:
<221> NAME/KEY: misc_feature
<222> LOCATION: (1)..(30)
<223> OTHER INFORMATION: n is a, c, g, or t

<400> SEQUENCE: 4
nnnnnnnnnn nnnnnnnnnn nnnnnnnnnn                                        30

<210> SEQ ID NO 5
<211> LENGTH: 3
<212> TYPE: DNA
<213> ORGANISM: Artificial Sequence
<220> FEATURE:
<223> OTHER INFORMATION: TCA region synthetic nucleotide

<400> SEQUENCE: 5

```
tca                                                                         3

<210> SEQ ID NO 6
<211> LENGTH: 33
<212> TYPE: DNA
<213> ORGANISM: Artificial Sequence
<220> FEATURE:
<223> OTHER INFORMATION: universal sequence synthetic oligonucleotide

<400> SEQUENCE: 6
actgacctca agtctgcaca cgagaaggct aga                                       33

<210> SEQ ID NO 7
<211> LENGTH: 12
<212> TYPE: DNA
<213> ORGANISM: Artificial Sequence
<220> FEATURE:
<223> OTHER INFORMATION: randomer cell tag region synthetic
      oligonucleotide
<220> FEATURE:
<221> NAME/KEY: misc_feature
<222> LOCATION: (1)..(12)
<223> OTHER INFORMATION: n is a, c, g, or t

<400> SEQUENCE: 7
nnnnnnnnnn nn                                                              12

<210> SEQ ID NO 8
<211> LENGTH: 30
<212> TYPE: DNA
<213> ORGANISM: Artificial Sequence
<220> FEATURE:
<223> OTHER INFORMATION: universal sequence synthetic oligonucleotide

<400> SEQUENCE: 8
gactcagcct ctgtgcgtcc ctactctacc                                           30

<210> SEQ ID NO 9
<211> LENGTH: 108
<212> TYPE: DNA
<213> ORGANISM: Artificial Sequence
<220> FEATURE:
<223> OTHER INFORMATION: oligodT molecule synthetic oligonucleotide
<220> FEATURE:
<221> NAME/KEY: misc_feature
<222> LOCATION: (1)..(30)
<223> OTHER INFORMATION: n is a, c, g, or t
<220> FEATURE:
<221> NAME/KEY: misc_feature
<222> LOCATION: (67)..(78)
<223> OTHER INFORMATION: n is a, c, g, or t

<400> SEQUENCE: 9
nnnnnnnnnn nnnnnnnnnn nnnnnnnnnn tcaactgacc tcaagtctgc acacgagaag          60
gctagannnn nnnnnnnga ctcagcctct gtgcgtccct actctacc                       108

<210> SEQ ID NO 10
<211> LENGTH: 23
<212> TYPE: DNA
<213> ORGANISM: Artificial Sequence
<220> FEATURE:
<223> OTHER INFORMATION: universal sequence synthetic oligonucleotide

<400> SEQUENCE: 10
aagcagtggt atcaacgcag agt                                                  23
```

```
<210> SEQ ID NO 11
<211> LENGTH: 9
<212> TYPE: DNA
<213> ORGANISM: Artificial Sequence
<220> FEATURE:
<223> OTHER INFORMATION: randomer molecule tag synthetic oligonucleotide
<220> FEATURE:
<221> NAME/KEY: misc_feature
<222> LOCATION: (1)..(9)
<223> OTHER INFORMATION: n is a, c, g, or t

<400> SEQUENCE: 11 nnnnnnnnn                                                                  9

<210> SEQ ID NO 12
<211> LENGTH: 7
<212> TYPE: DNA
<213> ORGANISM: Artificial Sequence
<220> FEATURE:
<223> OTHER INFORMATION: overhang region synthetic oligonucleotide
<220> FEATURE:
<221> NAME/KEY: misc_feature
<222> LOCATION: (5)..(7)
<223> OTHER INFORMATION: may be ribonucleotides

<400> SEQUENCE: 12 acgcggg                                                                    7

<210> SEQ ID NO 13
<211> LENGTH: 39
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(32)
<223> OTHER INFORMATION: n is a, c, g, or t
<220> FEATURE:
<221> NAME/KEY: misc_feature
<222> LOCATION: (37)..(39)
<223> OTHER INFORMATION: may be ribonucleotides

<400> SEQUENCE: 13
aagcagtggt atcaacgcag agtnnnnnnn nnacgcggg                                 39

<210> SEQ ID NO 14
<211> LENGTH: 23
<212> TYPE: DNA
<213> ORGANISM: Artificial Sequence
<220> FEATURE:
<223> OTHER INFORMATION: universal sequence synthetic oligonucleotide

<400> SEQUENCE: 14
ttcgtcacca tagttgcgtc tca                                                  23

<210> SEQ ID NO 15
<211> LENGTH: 7
<212> TYPE: DNA
<213> ORGANISM: Artificial Sequence
<220> FEATURE:
<223> OTHER INFORMATION: overhang region synthetic oligonucleotide

<400> SEQUENCE: 15 tgcgccc                                                                    7

<210> SEQ ID NO 16
<211> LENGTH: 81
<212> TYPE: DNA
```

```
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(32)
<223> OTHER INFORMATION: n is a, c, g, or t
<220> FEATURE:
<221> NAME/KEY: misc_feature
<222> LOCATION: (40)..(81)
<223> OTHER INFORMATION: n is a, c, g, or t

<400> SEQUENCE: 16
ttcgtcacca tagttgcgtc tcannnnnnn nntgcgcccn nnnnnnnnnn nnnnnnnnnn     60
nnnnnnnnnn nnnnnnnnnn n                                              81

<210> SEQ ID NO 17
<211> LENGTH: 78
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (37)..(48)
<223> OTHER INFORMATION: n is a, c, g, or t

<400> SEQUENCE: 17
tcaactgacc tcaagtctgc acacgagaag gctagannnn nnnnnnga ctcagcctct      60 gtgcgtccct actctacc                                                  78

<210> SEQ ID NO 18
<211> LENGTH: 75
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (34)..(45)
<223> OTHER INFORMATION: n is a, c, g, or t

<400> SEQUENCE: 18
actgacctca agtctgcaca cgagaaggct agannnnnnn nnnnngactc agcctctgtg    60
cgtccctact ctacc                                                     75

<210> SEQ ID NO 19
<211> LENGTH: 84
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(32)
<223> OTHER INFORMATION: n is a, c, g, or t
<220> FEATURE:
<221> NAME/KEY: misc_feature
<222> LOCATION: (40)..(81)
<223> OTHER INFORMATION: n is a, c, g, or t

<400> SEQUENCE: 19
ttcgtcacca tagttgcgtc tcannnnnnn nntgcgcccn nnnnnnnnnn nnnnnnnnnn     60
nnnnnnnnnn nnnnnnnnnn ntca                                           84

<210> SEQ ID NO 20
<211> LENGTH: 51
```

```
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (24)..(32)
<223> OTHER INFORMATION: n is a, c, g, or t
<220> FEATURE:
<221> NAME/KEY: misc_feature
<222> LOCATION: (40)..(51)
<223> OTHER INFORMATION: n is a, c, g, or t

<400> SEQUENCE: 20
ttcgtcacca tagttgcgtc tcannnnnnn nntgcgcccn nnnnnnnnnn n          51
```

METHODS AND COMPOSITIONS FOR TAGGING AND ANALYZING SAMPLES

CROSS-REFERENCE

This application is a continuation of U.S. patent application Ser. No. 14/776,177, filed on Sep. 14, 2015 entitled "METHODS AND COMPOSITIONS FOR TAGGING AND ANALYZING SAMPLES," now U.S. Pat. No. 10,058,839, which is a U.S. National Phase Application from PCT/US2014/029393, filed on Mar. 14, 2014 entitled "METHODS AND COMPOSITIONS FOR TAGGING AND ANALYZING SAMPLES," which claims the benefit of U.S. Provisional Application No. 61/801,785, filed Mar. 15, 2013, and U.S. Provisional Application No. 61/806,143, filed Mar. 28, 2013, all of which are incorporated herein by reference in their entireties.

BACKGROUND OF THE INVENTION

The analysis of nucleic acids and proteins in biological samples is an essential element of molecular biology. The ability to detect, discriminate, and utilize genetic and proteomic information allows sensitive and specific diagnostics as well as treatment.

The present invention provides for rapid tagging and analysis of nucleic acids and protein at the single cell level.

SUMMARY OF THE INVENTION

The present invention provides methods of tagging target oligonucleotides that include steps of (a) partitioning DNA into a plurality of compartments; (b) performing an in vitro transcription reaction on the DNA within the compartments, thereby obtaining compartments comprising RNA; (c) merging the interior of the compartments comprising RNA with the interior of a set of compartments comprising target oligonucleotides; (d) hybridizing the RNA to the target oligonucleotides; and (e) performing a reaction to attach a sequence corresponding to the RNA to the target oligonucleotides.

In some embodiments, the DNA is double stranded.

In some embodiments, the compartments are droplets within an oil-and-water emulsion.

In some embodiments, the target oligonucleotides include at least one target oligonucleotide comprising a cell tag and a molecule tag.

In some embodiments, the target oligonucleotides are DNA.

In some embodiments, the method may further include a step of partitioning the target oligonucleotides into the set of compartments before the merging of step (c).

In some embodiments, the method may further include a step of partitioning a set of cells into the set of compartments and lysing the cells in order to liberate cellular oligonucleotides before the merging of step (c). For example, the cellular oligonucleotides are the target oligonucleotides. Alternatively, the cellular oligonucleotides are cellular mRNA.

In some embodiments, the method may further include a step of conducting a reverse transcription on the cellular mRNA to generate cellular cDNA.

For example, the reverse transcription reaction is performed with a primer specific for a region of the genome. The region of the genome can be an immunoglobulin gene or a T-cell receptor gene.

For example, the reverse transcription reaction can be conducted within the set of compartments prior to the merging step.

Alternatively, the reverse transcription reaction can be conducted within the merged compartments.

In some embodiments, the target oligonucleotides are cellular cDNA.

In some embodiments, the reaction is a Rapid Amplification of cDNA Ends (RACE) reaction.

In some embodiments, the DNA is conjugated to a solid support. For example, the solid support is a bead.

The present invention also provides methods that include steps of (a) providing a plurality of beads comprising a plurality DNA oligonucleotides; (b) providing a plurality DNA oligonucleotides comprising a primer sequence, a universal sequence an adapter sequence and a cellular tag; (c) merging the beads of step (a) and the oligonucleotides of step (b) into a plurality of compartments such that each compartment comprises a single bead and a single oligonucleotide; (d) performing an amplification reaction on the oligonucleotides within the compartments, thereby obtaining a plurality of DNA oligonucleotides comprising the primer sequence, the universal sequence, the adapter sequence and the cellular tag; (e) performing an in vitro transcription reaction on the DNA within the compartments, thereby obtaining compartments comprising RNA the primer sequence, the universal sequence and cellular tag; (f) merging the interior of the compartments comprising RNA with the interior of a set of compartments comprising target oligonucleotides; (g) hybridizing the RNA to the target oligonucleotides; and (h) performing a reaction to attach a sequence corresponding to the RNA to the target oligonucleotides.

In some embodiments, the plurality of oligonucleotides on the bead includes a molecule tag.

The present invention further provides methods of tagging target oligonucleotides that include steps of (a) isolating a plurality of mRNA from a biological sample comprising a plurality of cell types; and (b) performing reverse transcription of the mRNA using a primer specific for the target oligonucleotide and a template switching oligonucleotide comprising a molecule tag, a universal sequence, and an adapter sequence to produce tagged target cDNA.

In some embodiments, the target cDNA is tagged at the 3'end.

In some embodiments, the target oligonucleotide is an immunoglobulin or T-cell receptor.

In some embodiments, the adapter sequence is specific to a sequencing platform.

In some embodiments, the molecule tag is an oligomer. For example, the oligomer is a randomer.

In some embodiments, the randomer is at least a 9 mer.

In some embodiments, the method further includes a step of amplifying the target cDNA using the universal sequence and a primer specific for the target oligonucleotide.

In some embodiments, the method may further include a step of sequencing the amplified cDNA.

Also provided are methods of determining the immune repertoire in a subject by (a) isolating a plurality of mRNA from a biological sample comprising a plurality of cell types; (b) performing reverse transcription of the mRNA using a immunoglobulin or T-cell receptor specific primers and a template switching oligonucleotide comprising a molecule tag, a universal sequence and an adapter sequence to produce molecule tagged immunoglobulin or T-cell receptor cDNA; (c) amplifying the cDNA using the universal sequence and a primer specific for the target oligonucleotide; (d) sequencing the cDNA to produce a plurality of sequencing reads; (e) grouping the sequence reads with the same molecule tag and clustering the sequences within the same group; and (f) building a consensus sequence for each cluster to produce a collection of consensus sequences wherein the consensus sequence is used to determine the diversity of the immune repertoire.

In some embodiments, the target cDNA is tagged at the 3'end.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13 depicts preparation of an oligonucleotide-conjugated bead and generation of a tag-bearing oligonucleotide from the bead.

FIG. 14 shows steps for tagging and analyzing mRNA.

FIG. 15 shows additional steps for tagging and analyzing mRNA.

FIG. 16 depicts examples of methods of partitioning and merging.

FIG. 17 depicts combinatorial properties for certain randomer tag lengths.

DETAILED DESCRIPTION OF THE INVENTION

I. Overview

Figure 1:
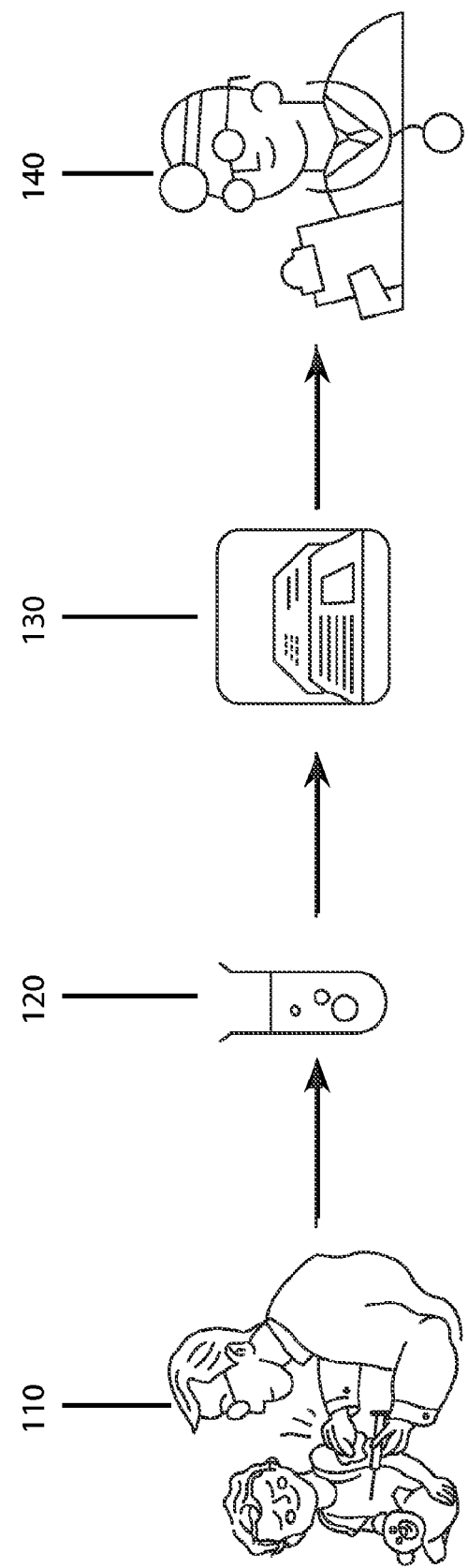
FIG. 1 is a schematic overview of the performance of an assay on a patient sample.
Figure 2:
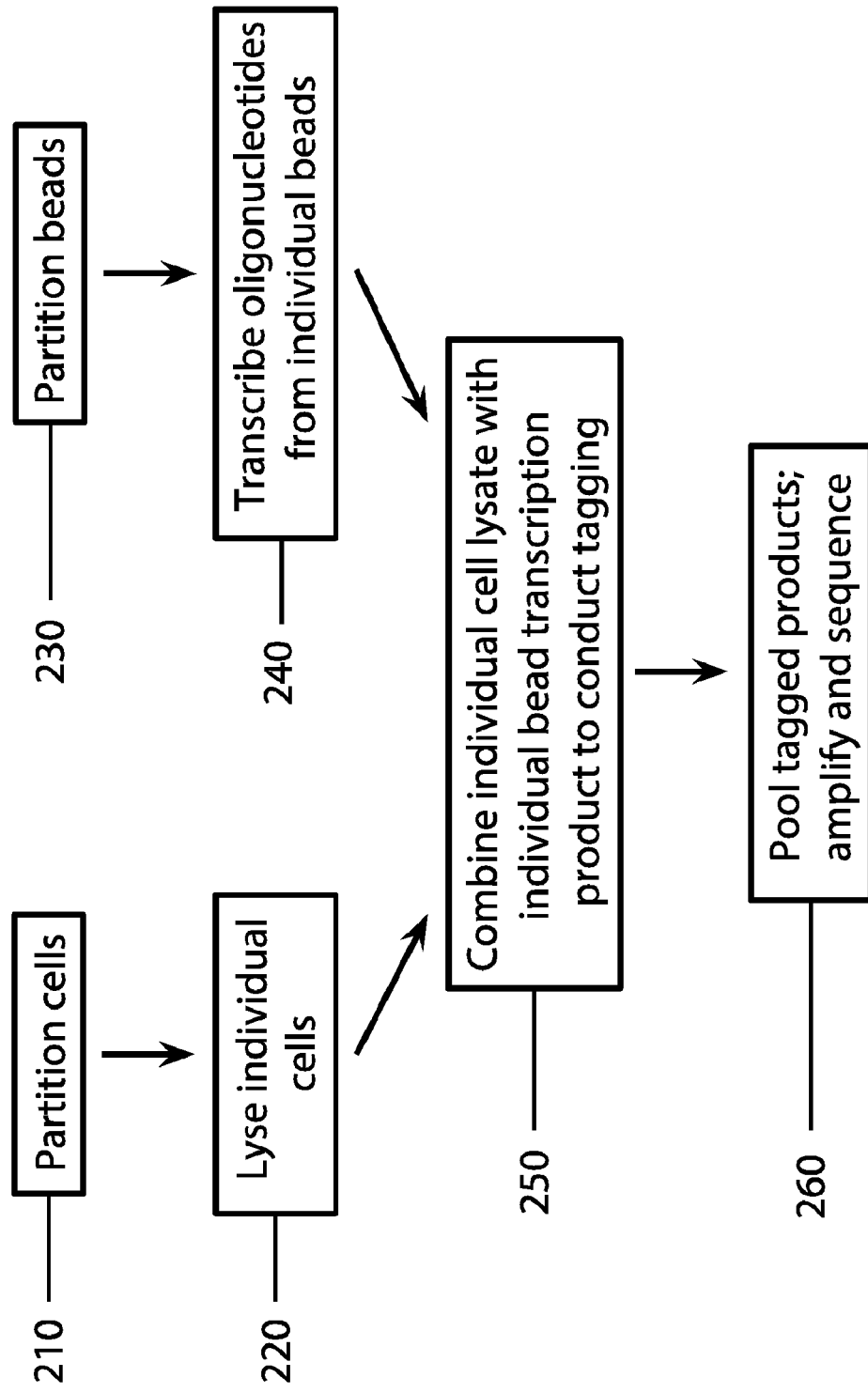
FIG. 2 is a schematic overview of an assay for tagging cells within a sample.

This disclosure provides methods and compositions for tagging molecules and subsequent analysis of the tagged molecules. In some cases, the disclosure provides methods and compositions for partitioning analytes (e.g., cells, polynucleotides) into individual partitions (e.g., droplets, wells, spots on arrays, etc.) and also provides methods and compositions for labeling the analytes within the partition.

In some cases, this disclosure generally relates to obtaining a sample (e.g. blood, saliva, tissue, cells) from a subject [110] (e.g. human, animal, plant, fungus, bacteria, population of cells, biofilm), partitioning and labeling the sample components with tagging molecules [120], processing and analyzing the labeled sample components [130], and/or reporting results from the analysis [140]. Cellular components such as DNA and RNA, individual cells or a population of cells may be partitioned. Cell population can include cells of similar function, such as for example, immune cells (e.g. B-cells or T-cells), cancer cells, or nerve cells. Moreover, a population of cells may be partitioned into cell partitions [210] and, separately, a population of beads with surface-bound oligonucleotides (e.g., DNA, dsDNA) may be partitioned within bead partitions [230]. The individual cells may be lysed within the cell partitions [220]. In some cases, the oligonucleotides are transcribed from the beads [240] such that RNA transcripts are produced in the bead partitions. In some cases, the RNA transcripts are reverse-transcribed into cDNA within the bead partitions; in some cases, the RNA transcripts are reverse-transcribed into cDNA within the bead partitions at a later step, such as after the contents of the bead partitions (e.g., droplets) are merged with the contents of another partition (e.g., a different droplet). The cell partitions may be combined with the bead partitions on a partition-by-partition basis [250]. Tagging reactions may then be conducted within the combined partitions in order to tag the cellular mRNA (or cDNA derived therefrom) with the oligonucleotides derived from the beads [250]. The tagged products may then be pooled, amplified, and sequenced [260].

The methods and compositions provided in this disclosure allow for tracking information sources and preserving the heterogeneity of information in a sample as it is analyzed. By labeling a sample at the individual component level, the resolution of the information can be maintained at the individual component level throughout the stages of analysis, regardless of subsequent merging or combining of the components. For example, a sample containing multiple cell types can be partitioned to a single cell type. Cell-types that can be partitioned into a single cell type include for example immune cells such as B-cells or T-cells. Alternatively, a sample containing multiple cell types can be partitioned into individual partitions containing single cells. By labeling the information-bearing molecules (e.g. DNA, RNA, protein) from a single cell type or a single cell, the individual partitions can then be merged for further analysis without loss of the single cell-level information resolution. The methods and compositions provided herein may also include additional labels, such as labels that enable quantification of the individual molecules within a partition. For example, a single partition may contain numerous unique labels, each with a different sequence that can be used to tag and quantify individual molecules within a partition.

The methods, compositions and kits provided herein are broadly applicable to a variety of life science-related fields, including biomedical research, drug discovery and development, and clinical diagnostics. Potential applications include gene expression profiling at the single cell type or single cell level for the detection and/or monitoring of cancer, autoimmune disease, viral infection, organ transplant rejection, and other diseases or disorders. The present disclosure may also be used to (a) analyze the immune repertoire of a subject, such as a subject with a particular disease or disorder; (b) elucidate intracellular signaling pathways; (c) validate therapeutic targets for drug discovery and development; and (d) identify or detect biomarkers, particularly biomarkers related to normal or diseased biological states. The present disclosure may also be used to analyze circulating cell-free DNA or RNA in order to predict, monitor, detect and/or diagnose conditions or diseases, including organ rejection.

The methods and compositions disclosed herein offer several important advantages over existing techniques for monitoring gene expression in cells or tissue. Importantly, the methods and compositions provided herein enable the monitoring and detection of gene expression in single cells, thereby eliminating the systematic errors and noise that may arise due to sampling of heterogeneous cell populations when collecting data using conventional techniques. The existence of heterogeneous cell populations in test samples may arise, for example, from asynchronous cell division in populations of cultured cells; or, in some cases, heterogeneity may be due to mixtures of different cell types present in tissue samples, biofilms, bioreactor samples, blood samples, biopsy samples or other complex samples. Another important advantage of the methods and compositions disclosed herein is the potential for eliminating or reducing errors caused by PCR amplification bias, for example, through the use of molecular tags that label different molecules within a sample. For example, if, when analyzed, the same molecular sequence is found to have two different tags, this may indicate that there were two copies of the molecule within the partition. This information may also be useful to discount results due to amplification errors. A third important advantage of the methods and compositions disclosed herein is the potential for expanding the range of biomarkers used to sort and classify cells. In addition to targeting gene sequences that code for the extracellular protein markers, the approach described herein enables the use of intracellular markers, for example gene sequences coding for transcription factors or cytokines, for cell sorting and classification in order to facilitate correlations between gene expression and cell function. The present disclosure thus offers an approach for obtaining higher quality genomic data from biological samples, and thus the potential for developing better therapeutics and improved detection of disease.

II. Assays

A. Labeling within Partitions

This disclosure provides methods and compositions for tagging analytes at a single component level, such as at the level of a single cell type or single cell. In some cases, analytes are partitioned into a set of partitions; labels are partitioned into a separate set of partitions, and the contents of individual partitions within each set are combined to enable labeling of the analyte.

Partitioning Analytes

A sample comprising analytes (e.g., cells) can be partitioned into a set of individual partitions (e.g., droplets or wells). In some cases, a partition within the set of individual partitions contains at most one analyte. In some cases, a partition within the set of individual partitions contains at most 2, 3, 4, 5, 6, 7, 8, 9, 10, 15, 20, 30, 40, 50, 60, 70, 80, 90, or 100 analytes. In some cases, a partition within the set of individual partitions contains, on average, one analyte. In some cases, a partition within the set of individual partitions contains, on average, 2, 3, 4, 5, 6, 7, 8, 9, 10, 15, 20, 30, 40, 50, 60, 70, 80, 90, or 100 analytes, or more. In some cases, the set of individual partitions comprises empty partitions. Often, the set of individual partitions comprises some empty partitions and some partitions comprising analytes (e.g., at most one analyte, at most two analytes, etc.). In some cases, an analyte comprises a plurality of components (e.g., a plurality of molecules). In some cases, a technique is applied to ensure that all of the partitions comprise at most one analyte; for example, the empty partitions (e.g., droplets) may be sorted out by a flow sorter.

Partitioning Tags

Tags or solid supports (e.g., beads) conjugated to tags can be partitioned into a set of individual partitions. In some cases, a partition within the set of individual partitions contains at most one tag or solid support (e.g., a bead) conjugated to a tag. In some cases, a partition within the set of individual partitions contains at most 2, 3, 4, 5, 6, 7, 8, 9, 10, 15, 20, 30, 40, 50, 60, 70, 80, 90, or 100 tags or solid supports (e.g., beads) conjugated to a tag. In some cases, a partition within the set of individual partitions contains, on average, one tag or solid support (e.g., bead) conjugated to a tag. In some cases, a partition within the set of individual partitions contains, on average, 2, 3, 4, 5, 6, 7, 8, 9, 10, 15, 20, 30, 40, 50, 60, 70, 80, 90, or 100 tags or solid supports (e.g., beads) conjugated to a tag. In some cases, the set of individual partitions comprises empty partitions. Often, the set of individual partitions comprises some empty partitions and some partitions comprising a tag (e.g., at most one tag, at most two tags, etc.). In some cases, a tag comprises a plurality of components (e.g., a plurality of molecules). In some cases, a technique is applied to ensure that all of the partitions comprise at most one tag or bead; for example, the empty partitions (e.g., droplets) may be sorted out by a flow sorter.

Labels or tags may be added to the contents of individual partitions in order to enable later identification of the particular analyte (e.g., cell) that is the source of a particular component (e.g., molecule). In some cases, the labels or tags are partitioned into a set of partitions; the partitions may then be used to label the partitioned analytes (e.g., cells).

The labels or tags may be conjugated to beads, for example, which are partitioned into the set of partitions (e.g., droplets). In some cases, material for generating labels or tags is partitioned into a set of partitions; the tags are then produced in the individual partitions and later used to label the analytes. For example, DNA tags (e.g., free DNA tags, DNA tags conjugated to beads) may be partitioned into individual partitions and then subsequently subjected to a polymerase chain reaction (PCR) to produce copies of the tags in solution within the partitions. The tags in solutions may then be used to directly label an analyte, or as a template that is used to label the analyte in a subsequent reaction. In some cases, the DNA tags (are subjected to an in vitro transcription reaction in order to produce RNA tags within the partitions. The RNA tags in solutions may then be used to directly label an analyte, or as a template that is used to label the analyte in a subsequent reaction such as a RACE reaction.

Intra-Partition Tagging

In some cases, the contents of the analyte and tag partitions described herein can be combined in order to facilitate labeling on a per-analyte (e.g., per-cell) basis. For example, if the partitions are droplets, individual droplets from an analyte set of droplets can be merged with individual droplets from a tag set of droplets in order to facilitate labeling of the analytes. Methods of combining contents of partitions are described elsewhere herein.

In some cases, a sample containing cells can be partitioned into individual partitions, each partition comprising cell(s). Tags can be applied to the analyte components (e.g., DNA, RNA, etc.) within a partition, so that each component within a partition is labeled with the same tag, such as a cell tag capable of identifying a particular cell. In some cases, tags can be applied to the analyte components (e.g., DNA, RNA, etc.) within a partition, so that a portion of the components within a partition is labeled with the same tag, such as a cell tag capable of identifying a particular cell. The tags may comprise a molecule tag, where each tag within a partition comprises a different molecule tag. In some cases, an individual tag may comprise both a cell tag and a molecule tag. The components within a partition may be labeled with tags, so that each analyte or analyte component in a partition is labeled with a different molecule tag label. The components within a partition may be labeled with tags, so that each analyte or analyte component in a partition is labeled with an identical cell tag. The components within a partition may be labeled with tags, so that each analyte or analyte component in a partition is labeled with a different molecule tag and an identical cell tag.

Figure 8:
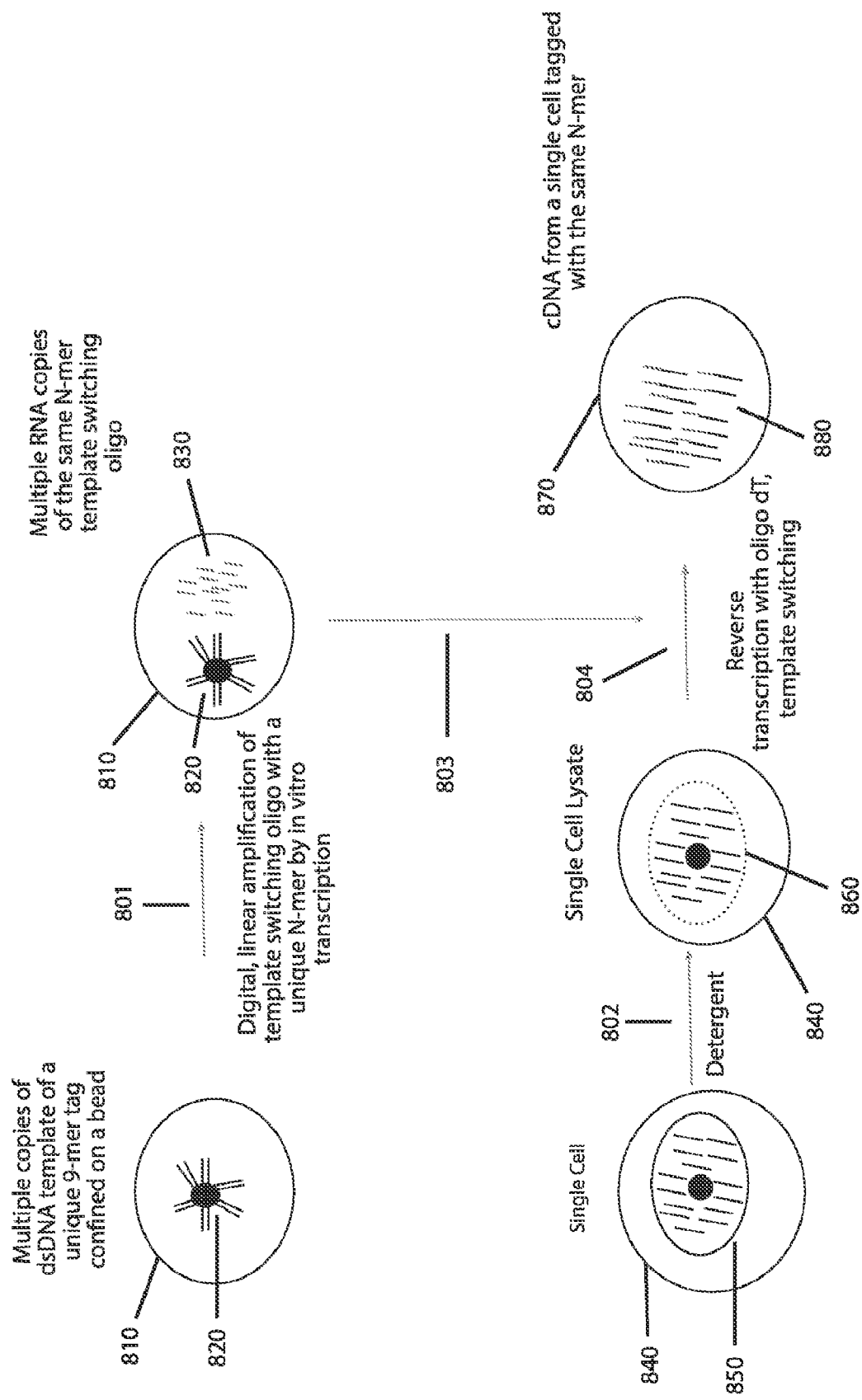
FIG. 8 depicts tagging and analysis of analytes within partitions that may be merged.
Figure 9:
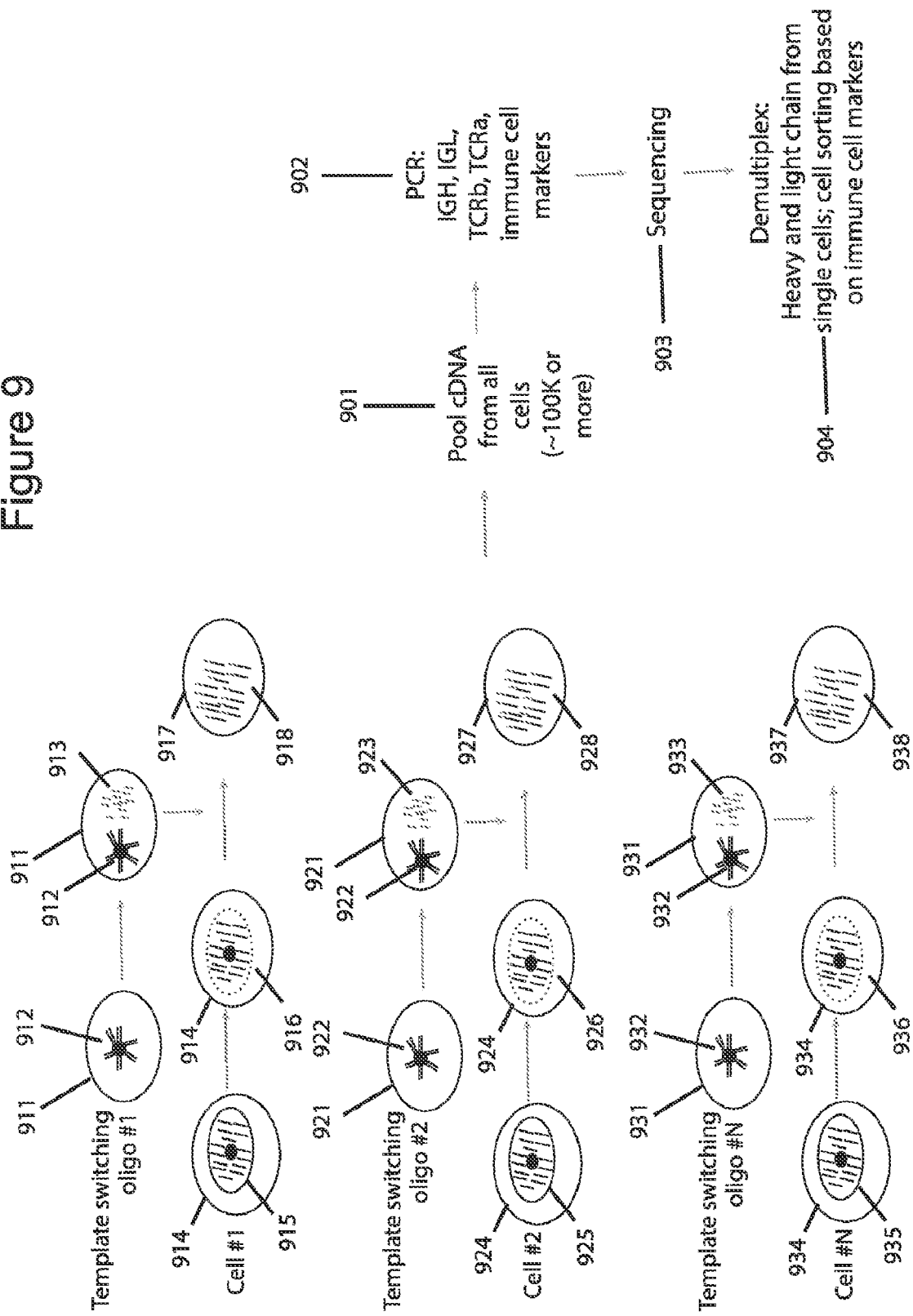
FIG. 9 depicts multiplexed tagging and analysis.

FIG. 8 depicts exemplary methods provided herein. In some cases, a solution comprising beads conjugated to nucleic acids [820] is partitioned into droplets [810]. In some cases, the droplets contain at most one bead. The nucleic acids may be double-stranded DNA (dsDNA), single-stranded DNA (ssDNA), RNA, or a combination DNA and RNA. The nucleic acids may comprise a unique tag sequence (e.g. a 9-mer randomer). By "randomer" as used herein it is meant an oligonucleotide with randomly synthesized bases. When the beads are conjugated to dsDNA, in vitro transcription [801] may then be used to produce RNA transcripts from the tag dsDNA conjugated to the beads [830]. The oligonucleotides can be template switching oligonucleotides. In some cases, a solution comprising cells [850] is partitioned into droplets [840]. In some cases, the droplets contain at most one cell. Cells may be lysed [802]. Lysis can be performed by adding a lysis solution, buffer, or detergent to the cell, by sonication, by shear, by freezing and thawing, by heating, by electrical lysis, by grinding, or by any other appropriate method. Addition of lysis solution, buffer, or detergent can be performed by droplet injection, by droplet merging, or by any other appropriate method.

Droplets containing cell lysate [860] may then be merged [803] with droplets containing amplified oligonucleotides. Alternatively, the material within the droplets may be lysed following merging. Droplet merging may be conducted by any appropriate means, including passive droplet merging (e.g. at a microfluidic junction) and active droplet merging (e.g. electric, magnetic, thermal, or optical means). Alternatively, cell lysis may be conducted after droplet merging. Reverse transcription [804] with oligonucleotides and cell lysate may then be performed in the merged droplet [870] to produce cDNA [880] from a single cell tagged with the same unique tag sequence.

In some cases, oligonucleotides derived from many cells may be tagged in parallel, for example on a high-throughput basis. A solution comprising beads with surface-bound nucleic acids and a solution comprising cells may each be partitioned into droplets. In some cases, the bead droplets ([911], [921], [931]) comprise a bead ([912], [922], [932]) and the cell droplets ([914], [924], [934]) comprise a cell ([915], [925], [935]). The nucleic acids may be double-stranded DNA, single-stranded DNA, RNA, or a combination DNA and RNA. The nucleic acids may comprise a unique tag sequence (e.g. a 9-mer randomer). In vitro transcription may then be used to amplify oligonucleotides with a tag sequence ([913], [923], [933]). The oligonucleotides can be template switching oligonucleotides. Cells may be lysed. Lysis can be performed by adding a lysis solution, buffer, or detergent to the cell, by sonication, by shear, by freezing and thawing, by heating, by electrical lysis, by grinding, or by any other appropriate method. Addition of lysis solution, buffer, or detergent can be performed by droplet injection, by droplet merging, or by any other appropriate method. Droplets containing lysate ([916], [926], [936]) may then be merged with droplets containing amplified oligonucleotides. Droplet merging may be conducted by any appropriate means, including passive droplet merging (e.g. at a microfluidic junction) and active droplet merging (e.g. electric, magnetic, thermal, or optical means). Alternatively, cell lysis may be conducted after droplet merging. Reverse transcription with oligonucleotides and cell lysate may then be performed in the merged droplets ([917], [927], [937]) to produce cDNA ([918], [928], [938]), where the cDNA in each droplet is from a single cell and is tagged with the same unique tag sequence. After labeling, the cDNA from all cells may be pooled [901]. The number of cells may be at least 10, at least 100, at least 1000, at least 10,000, or at least 100,000. PCR may then be conducted on the pooled cDNA [902]. The PCR may specifically target genes or regions of interest for sequencing. The genes or regions of interest may comprise immunoglobulin heavy chain (IgH), immunoglobulin light chain (IgL), T-cell receptor beta (TCRb), T-cell receptor-alpha (TCRa), or immune cell markers. Amplified DNA may then be sequenced [903]. Information from sequencing may then be demultiplexed [904] based on the tag sequences.

The methods provided herein may result in the production of cDNA constructs which contain genetic information from cell mRNA and tag information from tags. The tag information may comprise cell tag information. The tag information may comprise molecule tag information.

Partitions may be merged into one total population subsequent to the generation of labeled molecules within the partitions. After merging, any desired analysis may be performed on the bulk population of molecules without loss of information resolution.

In some cases, a total population of cDNA molecules comprising mRNA information, cell tag information, and molecule tag information may be amplified by universal PCR to increase the total number of cDNA constructs. Sequence specific PCR may then be performed to produce sequencing-compatible DNA molecules containing cell tag information, molecule information, and genetic information of interest. By sequencing these molecules, genetic information may then be traced backwards and associated with original cells and molecules by use of tag information.

III. Tags

The methods, compositions, and kits described herein include the use of tags to identify individual sub-populations of a sample, such as cells or molecules originating from individual cells, (cell tags) and specific analytes, such as oligonucleotide sequences, contained within the individual sub-populations (molecule tags). In general, tags may comprise oligonucleotides, DNA, RNA, polypeptides, antibodies, and/or other proteins. In particular, this disclosure describes tags comprised of oligonucleotides. In some cases, the oligonucleotide comprises cell tags. In some cases, the oligonucleotides comprises molecule tags. In some cases, an oligonucleotides comprises both molecule tags and cell tags. In some cases, the oligonucleotides comprises additional sequences.

Cell Tags

Cell tags may be unique N-mer sequences that are used to identify the individual sub-population, such as the cell, from which a given component, such as gene expression product or oligonucleotide sequence (mRNA, DNA), was derived. Cell tags may comprise random N-mer oligonucleotide sequences (one unique identifier sequence per cell) that may be incorporated into cDNA constructs that include promoter sequences, adaptor sequences, and/or primer sequences that enable downstream amplification and sequencing of all or part of the gene products or oligonucleotide sequences that are being targeted. Each specific N-mer sequence may serve as a unique identifier for an individual cell, and may be incorporated into cDNA constructs using any of the several methods described herein.

The set of random N-mers used as cell tags in the examples disclosed herein are 9 bases long, but this length may be varied if a larger (or smaller) number of unique identifiers is required. In general, the length of the random N-mer used as a cell tag may range from 2 bases to 100 bases long, or may be more than 2, 3, 4, 5, 6, 7, 8, 9, 10, 11, 12, 13, 14, 15, 20, 30, 40, 50, 60, 70, 80, 90, 100, 110, 120, 130, 140, 150, 160, 170, 180, 190, or 200 bases long. Preferentially, the random N-mer used as a cell tag is at least 4 bases long and at most 14 bases long. For a random 9-mer, there are $2.62 \times 10^5$ possible base combinations available for tagging individual cells. Examples of combinatorial properties for a given randomer length are provided in FIG. 17. In some examples presented below, the cell tag sequence initially consists of a DNA sequence, and is subsequently converted to a complementary RNA sequence incorporated into a template switching oligonucleotide using an in vitro transcription reaction. In other examples, the cell tag sequence could be introduced directly as RNA, for example, as part of a library of template switching oligonucleotides synthesized using combinatorial solid-state synthesis techniques. In many cases, the cell tag serves as both an identifier for the cell in which a given sequence is expressed, and as part of a template switching primer that is used to incorporate a collection of molecule tags and other promoter, primer, and/or adaptor sequences into the final cDNA library.

Molecule Tags

Molecule tags can comprise unique N-mer sequences that are used to identify the individual molecules (gene sequences, oligonucleotides, mRNA, DNA) that were derived from a given individual cell. Molecule tags can comprise random N-mer sequences (one unique identifier per molecule) that may be incorporated into cDNA constructs that include promoter sequences, adaptor sequences, and/or primer sequences that enable downstream amplification and sequencing of all or part of the gene products or oligonucleotide sequences that are being targeted. Each specific N-mer sequence may serve as a unique identifier for the target sequence to be detected, and is incorporated into cDNA constructs using any of the several methods described below. The set of random N-mers used as molecule tags in some of the examples disclosed herein are 9 bases long, but again, may be adjusted in length to provide the number of unique molecule identifiers required for a given application. In general, the length of the random N-mer used as a molecule tag may range from 2 bases to 100 bases long, or may be more than 2, 3, 4, 5, 6, 7, 8, 9, 10, 11, 12, 13, 14, 15, 20, 30, 40, 50, 60, 70, 80, 90, 100, 110, 120, 130, 140, 150, 160, 170, 180, 190, or 200 bases long. Preferentially, the random N-mer used as a molecule tag is at least 4 bases long and at most 14 bases long. Depending on the specific set of tagging reactions performed, the molecule tag may consist of a DNA sequence, an RNA sequence, or may be converted from one to another during the course of the tagging procedure by means of performing in vitro transcription or reverse transcription reactions. In some cases, the molecule tag serves as both an identifier for the target sequence of interest, and as part of a template switching primer that is used to incorporate other promoter, primer, and/or adaptor sequences into the final cDNA library.

Additional Oligonucleotide Sequences

In some cases, the additional nucleotide sequences comprise primers, such as PCR primers or reverse transcription primers or transcription promoter sequences. The oligonucleotide constructs used to incorporate cell and molecular tags into the cDNA library typically include primer sequences for the purpose of initiating in vitro reverse transcription reactions. Any of a number of known primer sequences may be used, for example, sequence-specific primers, oligo(dT) primers, random hexamer primers, or random decamer primers. In some cases, a general reverse transcriptase primer, for example, a poly-dT primer that complements the 3' poly-A tail found on eukaryotic mRNA, is used to reverse transcribe all mRNA expressed in a cell. In other cases, the reverse transcriptase primer may be designed for specific gene sequences in order to perform sequence-specific reverse transcription.

In some cases, the oligonucleotides may comprise universal primer sequences. The oligonucleotide constructs used to incorporate cell and molecule tags into the cDNA library may include universal primer sequences for the purpose of initiating PCR amplification of the oligonucleotide construct. Any of a number of known universal primer sequences may be used, including the T7 universal primer sequence, or the SP6 universal primer sequence.

In some cases, the oligonucleotides may comprise promoter sequences. The oligonucleotide constructs used to incorporate cell and molecular tags into the cDNA library may also include promoter sequences for the purpose of initiating polymerase reactions. Any of a number of well-known promoter sequences, for example, the T3 promoter sequence, or the T7 promoter sequence may be used.

The oligonucleotide constructs used to incorporate cell and molecular tags into the cDNA library may also include adaptor sequences, which can be used, for example, for the purpose of facilitating sequencing of the final cDNA library on commercial sequencing platforms. Any of a number of known adaptor sequences may be used, e.g. those recommended by Illumina, Life Technologies, Pacific Biosciences, or others.

Attachment of Oligonucleotides onto a Solid Support

A variety of techniques may be used to incorporate cell and molecule tags onto a solid support.

In one approach, a single-stranded primer sequence (for example, the T7 promoter sequence) is covalently attached to a bead, and a PCR reaction using a complementary cell tag construct is performed within a compartment containing the bead to create double-stranded DNA template on the bead. The double-stranded DNA on the bead then serves as the template for subsequent in vitro transcription and PCR reactions.

In an alternative approach, a single-stranded primer sequence that incorporates a molecule tag (for example, a random N-mer sequence) is covalently attached to the bead, and a PCR reaction using a complementary cell tag construct is performed within a compartment containing the bead to create double-stranded DNA template on the bead. Again, the double-stranded DNA on the bead then serves as the template for subsequent in vitro transcription and PCR reactions.

In some approaches, the initial primer is covalently attached to the bottom surface of a microwell, and the PCR reaction using a complementary cell tag construct is performed within the well to create double-stranded DNA template molecules attached to the bottom of the well. In yet other approaches, the initial primer is covalently attached to a microarray substrate, and the PCR reaction using a complementary cell tag construct is performed within a droplet or layer of liquid in contact with the microarray to create double-stranded DNA template molecules attached to the microarray substrate. In some cases, the PCR reaction using the appropriate primers may be performed in solution, for example, within the confines of a droplet of liquid or within a microwell.

Solid Supports

Suitable solid phase carriers include, but are not limited to, other particles, fibers, beads and or supports which have an affinity for DNA, RNA, double-stranded DNA, single stranded DNA, ssRNA and which can embody a variety of shapes, that are either regular or irregular in form, provided that the shape maximizes the surface area of the solid phase, and embodies a carrier which is amenable to microscale manipulations An example of a suitable bead is a porous or nonporous polymer bead comprised of a copolymer of vinyl aromatic monomers. Examples of vinyl aromatic monomers include styrene, alkyl substituted styrene, alpha-methylstyrene, and alkyl substituted alpha-methylstyrene.

Another example of a suitable bead is a porous or nonporous particle such as silica, silica carbide, silica nitrite, titanium oxide, aluminum oxide, zirconium oxide which is modified to have a hydrophobic surface.

In some aspects the solid surface has a functionalize surface such that the surface is coated with moieties which reversibly bind nucleic acid (e.g., DNA, RNA). One example is a surface which is coated with moieties which each have a free functional group which is bound to the amino group of the amino silane or the microparticle; as a result, the surfaces of the microparticles are coated with the functional group containing moieties. The functional group acts as a bioaffinity adsorbent for polyalkylene glycol precipitated DNA. In one embodiment, the functional group is a carboxylic acid. A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface. Suitable solid phase carriers having a functional group coated surface that reversibly binds nucleic acid molecules are for example, magnetically responsive solid phase carriers having a functional group-coated surface, such as, but not limited to, amino-coated, carboxyl-coated and encapsulated carboxyl group-coated paramagnetic microparticles.

IV. Template Switching Oligonucleotides

Tags may be delivered by template switching oligonucleotides. Template switching oligonucleotides may be RNA or DNA. Template switching oligonucleotides may comprise a hybridization region and a template region. The hybridization region can comprise any sequence capable of hybridizing to the target. In some cases, the hybridization region comprises a series of G bases to complement the overhanging C bases at the 3' end of a cDNA molecule, which result from the terminal transferase activity of reverse transcriptase. The series of G bases may comprise 1 G base, 2 G bases, 3 G bases, 4 G bases, 5 G bases, or more than 5 G bases. The template region can comprise any sequence to be incorporated into the cDNA by primer extension reaction. In some cases, the template region comprises one or more tag sequences. The template region can contain one tag sequence, two tag sequences, three tag sequences, or more than three tag sequences. The template region may comprise a molecule tag region and a cell tag region.

Template switching oligonucleotides may further comprise additional regions. In some cases, the template switching oligonucleotide comprises one or more sequencing adaptor sequences or partial sequencing adaptor sequences. The sequencing adaptor sequence may be an Illumina adaptor sequence. The sequencing adaptor sequence may be a 454 adaptor sequence. The sequencing adaptor sequence may be a SOLiD adaptor sequence. In some cases, the template switching oligonucleotide comprises one or more universal sequences. Universal sequences may be used for primer binding for universal PCR or other reactions.

The template switching oligonucleotide (e.g., RNA oligonucleotide) may be incorporated into the cDNA sequence during the extension reaction of the reverse transcription. The hybridization region allows the template switching oligonucleotide to hybridize to the cDNA. Once the reverse transcriptase enzyme reaches the end of the mRNA, it switches to the template switching oligonucleotide and incorporates its sequence into the cDNA as well. See, e.g., FIG. 3.

Figure 3:
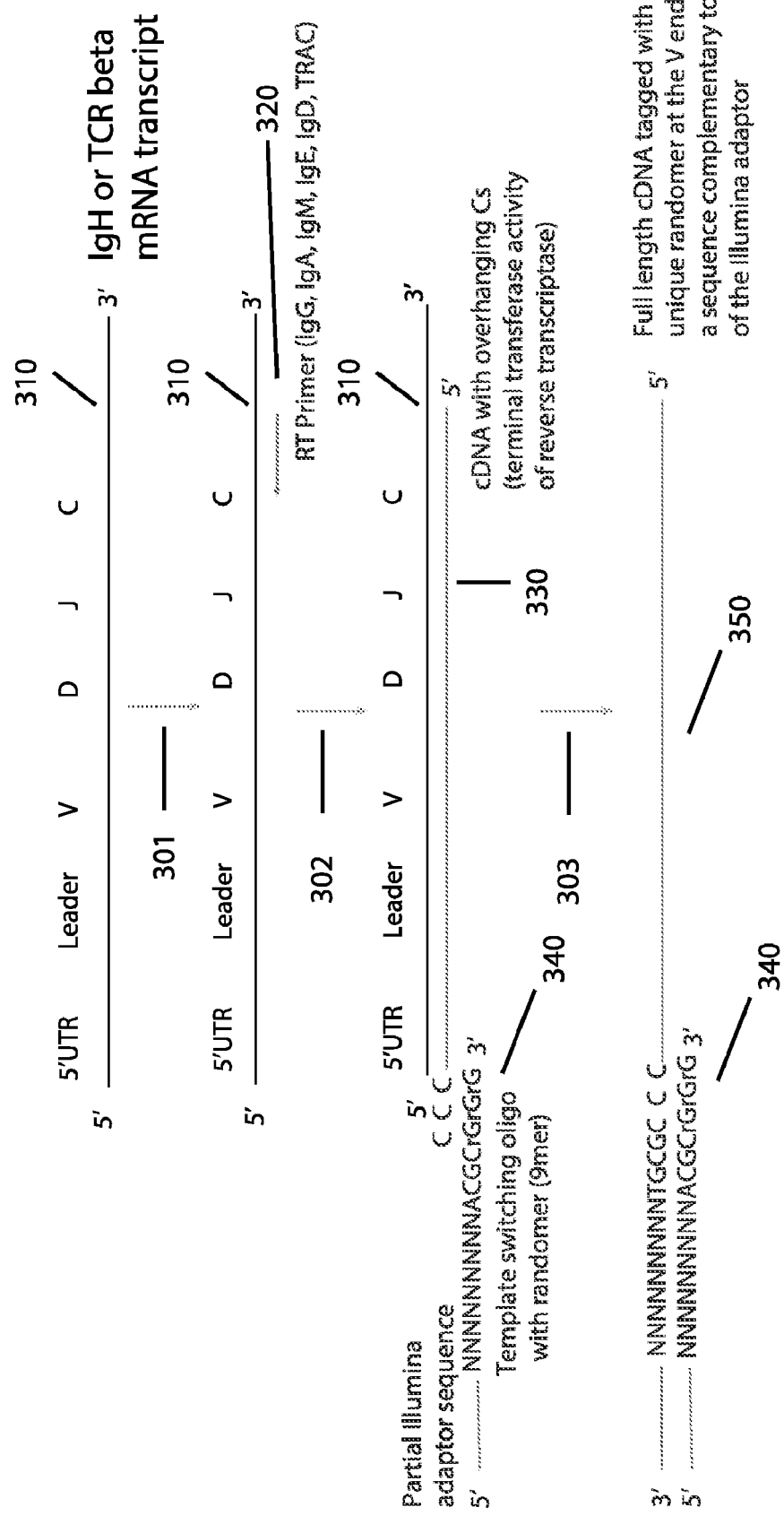
FIG. 3 depicts steps that may be involved in a Rapid Amplification of cDNA Ends (RACE) assay.
Figure 4:
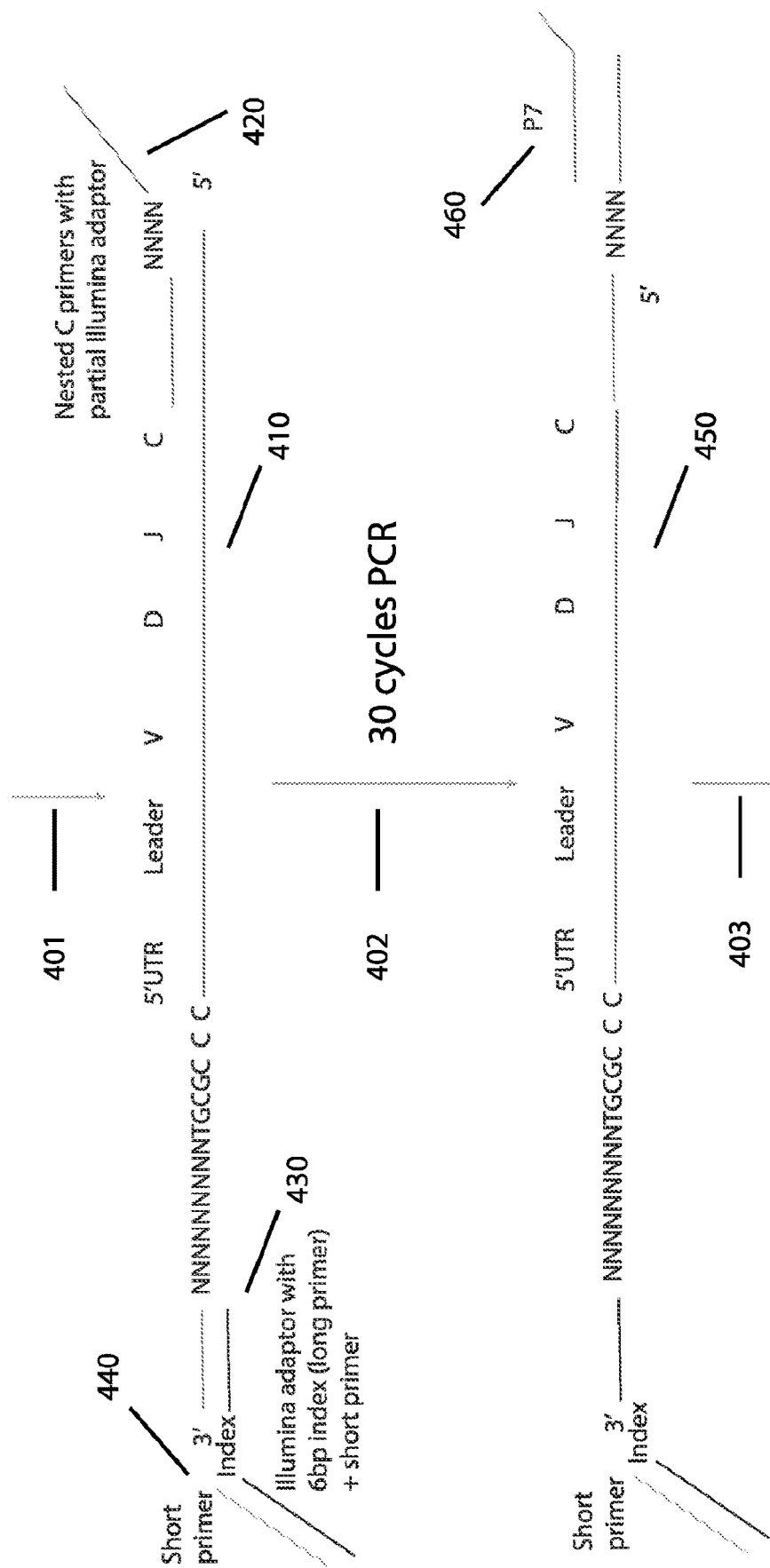
FIG. 4 depicts additional steps that may be involved in a RACE assay.
Figure 5:
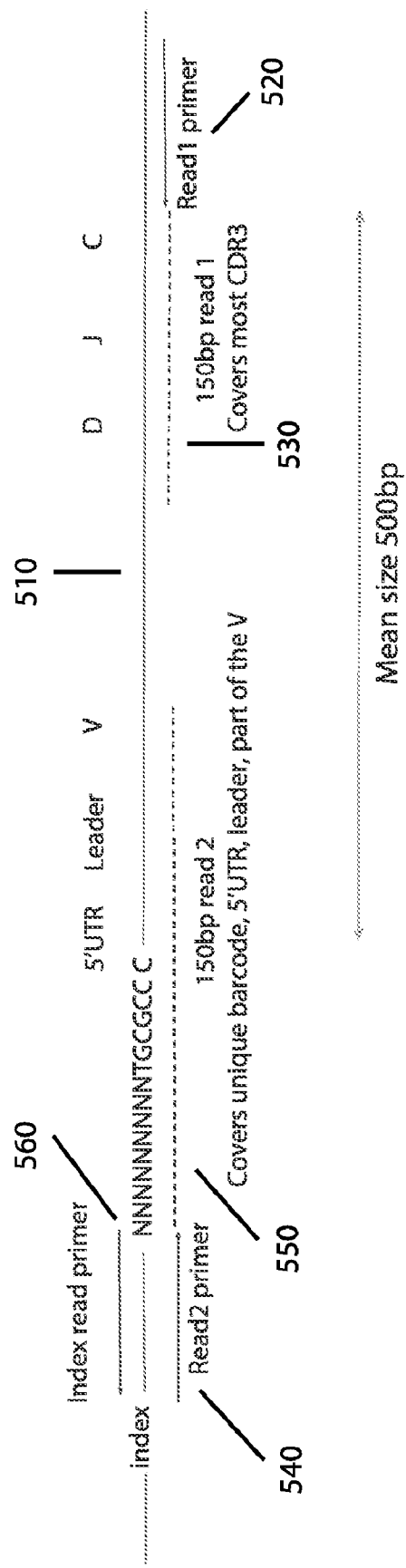
FIG. 5 depicts additional steps that may be involved in a RACE assay.
Figure 6:
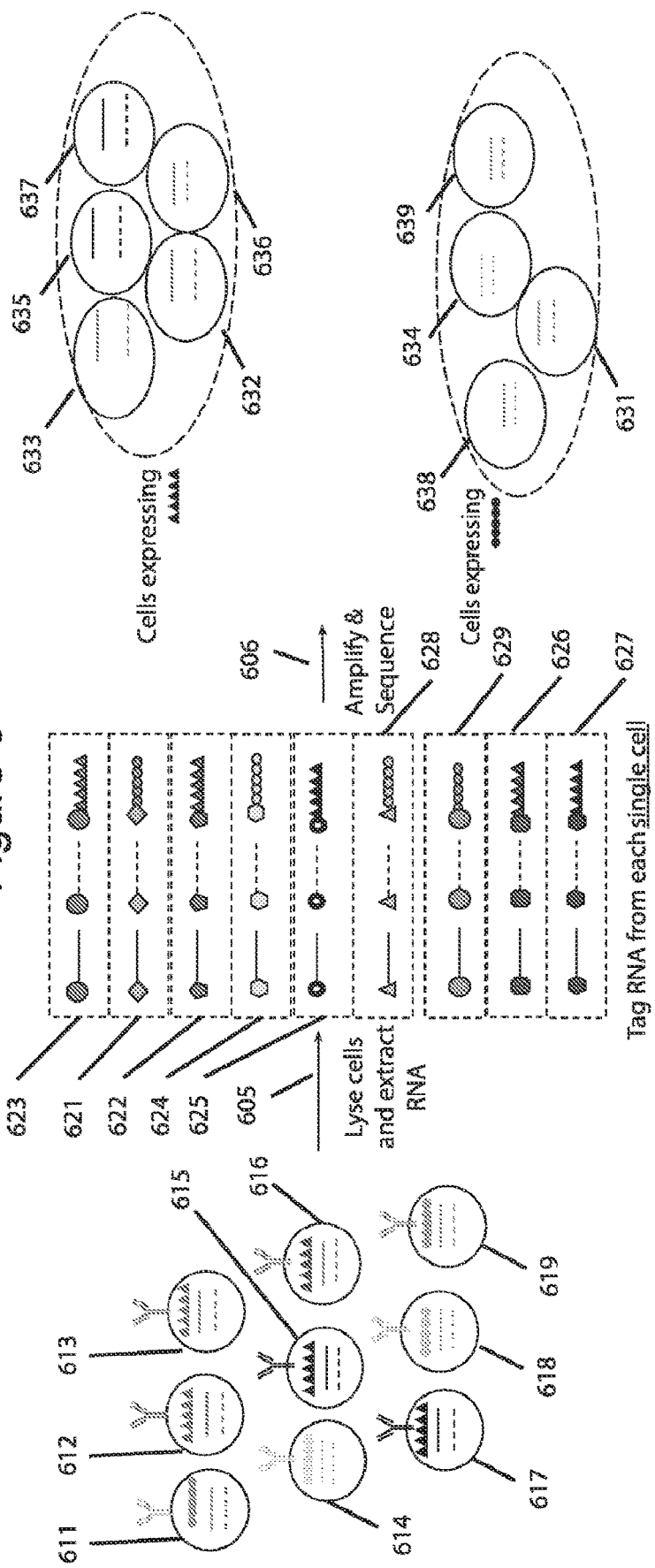
FIG. 6 depicts performance of an immune repertoire assay on a population of cells.
Figure 7:
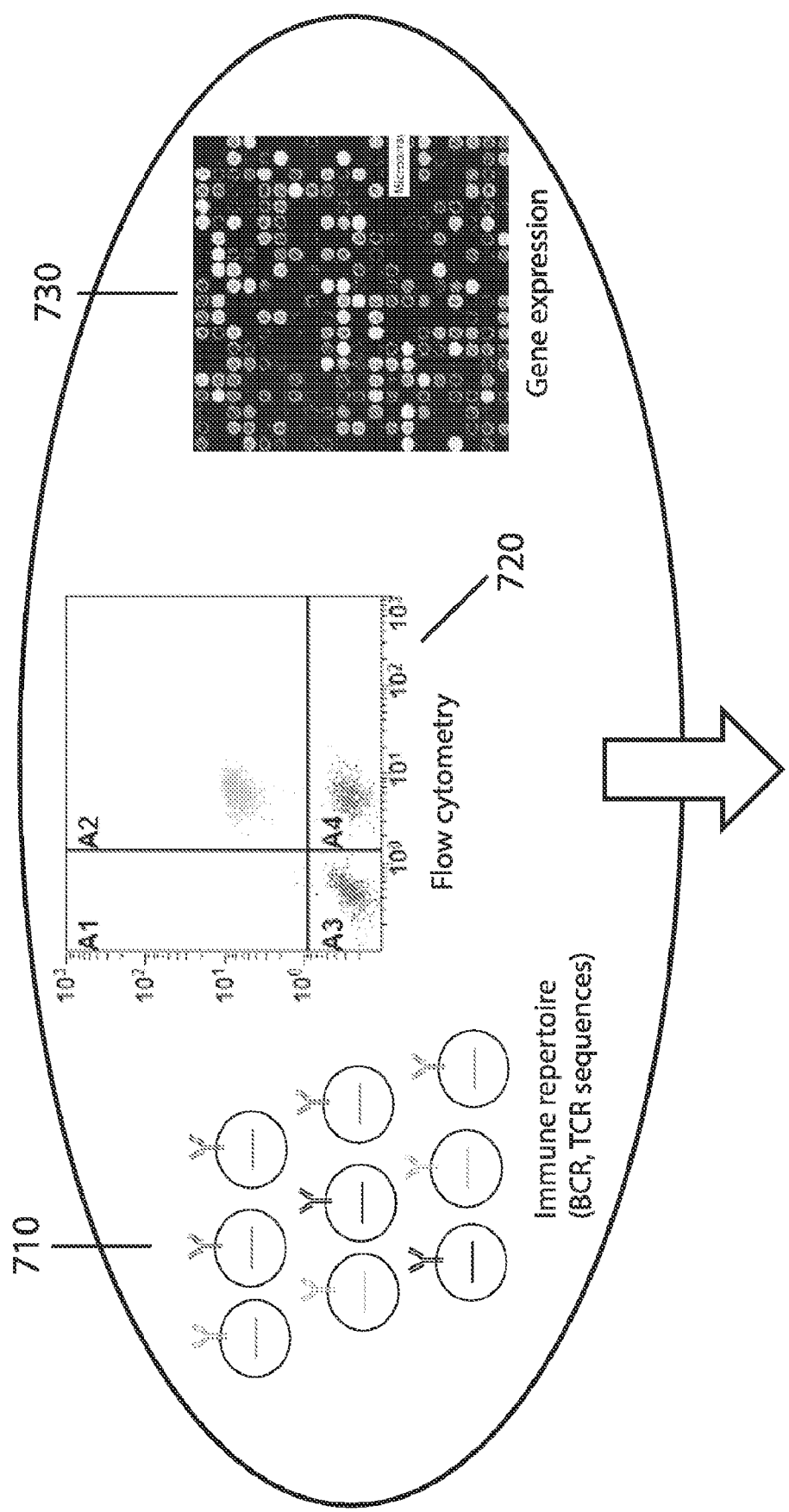
FIG. 7 depicts flow cytometry and gene expression assays for the immune repertoire.

The assays provided herein can comprise a Rapid Amplification of cDNA Ends (RACE) assay as depicted, for example, in FIGS. 3-5. In some cases, the RACE assay may be performed on mRNA transcripts [310] from a cell. The mRNA transcript can be from a variety of genes, including genes related to immune function, such as IgH or TCR beta. In some cases, the mRNA transcript comprises six regions: a 5' untranslated region (5' UTR), a leader region, a V region, a D region, a J region, and a C region. Reverse transcription (RT) primers [320] may then be added [301]. In some cases, the RT primers can be specific for the heavy chain constant region of an immunoglobulin, e.g. IgG, IgA, IgM, IgE, or IgD, kappa (IgK) and lambda (IgL) light chain regions of a immunoglobulin, T cell receptor alpha constant regions (TRAC) and or T cell receptor beta constant regions (TRBC). Reverse transcriptase can then be used to perform reverse transcription [302] of the mRNA, resulting in cDNA [330] with overhanging C bases from the terminal transferase activity of the reverse transcriptase.

Template switching oligonucleotides [340] may then be added, switching the template molecule from the original mRNA to the cDNA. In some cases, the template switching oligonucleotide comprises three regions: a partial sequencing adaptor sequence (i.e., a universal sequence to the 3' end), a randomer molecule tag sequence, and a homopolymerice tail (i.e., G base region to complement the overhanging C bases of the cDNA). The partial sequencing adaptor sequence may be a partial Illumina adaptor sequence. The randomer molecule tag sequence may consist of nine random bases (9mer). The cDNA can then be extended [303] to include the template switching oligonucleotide sequence, resulting in a full length cDNA [350]. In some cases, the full length cDNA comprises a unique randomer molecule tag sequence at the V end and a sequence complementary to part of a sequencing adaptor sequence. The sequencing adaptor sequence can be an Illumina adaptor sequence.

Additional primers may then be added [401]. In some cases, three additional primers are added, comprising: nested C primers with a partial sequencing adaptor sequence [420], a sequencing adaptor sequence with a 6 base pair index [430] referred to as a long primer, and a short primer [440]. The sequencing adaptor sequences can be Illumina adaptor sequences. PCR may then be conducted [402] to produce amplified cDNA [450] which incorporates the primer sequences. In some cases, the PCR is conducted for 30 cycles. Additional primers may then be added. In some cases, one additional primer is added, comprising a full-length sequencing adaptor sequence [460]. The sequencing adaptor sequence can be an Illumina adaptor sequence, such as P7. PCR may then be conducted [403] to add on the full-length adaptor sequence. In some cases, the PCR is conducted for 8 cycles.

The resulting cDNA products [510] may then be sequenced and analyzed. In some cases, this is accomplished by sequencing. The sequencing may be performed with the use of read primers. In some cases, three read primers are used, comprising: a first read primer (Read1) [520], with a 150 base pair read area [530] covering most of the CDR3 region, a second read primer (Read2) [540], with a 150 base pair read area [550] covering the unique randomer molecule tag barcode sequence, the 5'UTR, the leader region, and part of the V region, and an index read primer [560], with a read area covering the index region. In some aspects the read length is 50, 100, 150, 200, 250, 500, 750, 1000, 1250 or 1500 base pairs. The cDNA products may be analyzed by other techniques, including hybridization probes.

The RACE assay may be 5' RACE or 3' RACE. In some cases, the sequencing is performed from linear cDNA products. In some cases, the sequencing is performed from circularized cDNA products. Circularized cDNA products may be produced by melting and circularizing, that is, the 3' and 5' ends of the linear DNA are brought together and bonded (e.g. by a circular ligase enzyme such as CircLigase™, EPICENTRE® Biotechnologies).

V. Reactions

The methods and compositions provided in this disclosure can comprise one or more reactions involved in performing analysis. The reactions can comprise sample preparation such as cell lysis, tag production such as in vitro transcription, tagging such as reverse transcription with template switching oligonucleotides, analyte amplification such as PCR, and analysis such as sequencing.

Cell Lysis

Following partitioning of cells into individual partitions, the cells may be lysed to release the intracellular contents, including RNA, DNA, proteins, and other intracellular components. The lysis reaction may be performed using any number of well-known techniques, for example by the addition of a detergent, addition of a lysis solution or hypotonic buffer, use of mechanical agitation or sonication, repeated cycles of freezing and thawing, or by any other appropriate method. Addition of lysis solutions, buffers, or detergents can be performed by conventional liquid dispensing methods, by droplet injection or merging techniques, or by any other appropriate method. Partitions containing cell lysate [860] may subsequently be merged [803] with partitions containing tags prior to performing downstream reactions. In some cases, lysis can be performed prior to merging the contents of the partition with another partition, such as a partition containing tag. In some cases, lysis can be performed after merging the contents of a partition with other partitions, such as partitions containing tags.

In Vitro Transcription.

In vitro transcription reactions may be used to convert DNA template molecules into RNA transcripts. The DNA template molecules used in the methods and compositions disclosed herein may be designed to contain promoter sequences for facilitating in vitro transcription. The DNA template molecules may comprise random or unique N-mer tagging sequences, and may also include primer and adaptor sequences for facilitating downstream amplification and sequencing reactions. The products of in vitro transcription reactions in the present method are RNA template switching oligonucleotides comprised of the said appropriate primer, adaptor, and/or tag sequences. In some cases, double-stranded DNA templates bound to beads are transcribed to produce RNA constructs comprising template switching oligonucleotides, which may include primer, adaptor, and/or random or unique N-mer cell tag sequences, random or unique N-mer molecule tag sequences, or both random or unique N-mer cell tag and N-mer molecule tag sequences. Alternatively, in vitro transcription may be used with free template DNA to create the RNA template switching constructs in solution.

In some cases, in vitro transcription reactions may be performed prior to combining DNA template sequences with cell lysates or other biological samples. In some cases, in vitro transcription reactions may be performed after combining DNA template sequences with cells, or material derived from a cell (e.g., polynucleotides, polypeptides, etc.), or other biological samples. DNA templates used in the in vitro transcription reaction can comprise a promoter sequence for facilitating the transcription reaction. Any number of known promoter sequences may be used, for example, the T3 RNA polymerase promoter sequence, T7 RNA polymerase promoter sequence, or any other suitable RNA polymerase promoter sequence. The transcription reaction may be performed under the appropriate reaction conditions using any appropriate in vitro transcription system, for example, the T3 RNA polymerase system, which includes the appropriate transcriptase (T3 RNA polymerase), ribonucleotide triphosphates, and buffer components (for example, dithiothreitol and magnesium ions).

The in vitro transcription assays can be designed so that all of the oligonucleotides present in a sample are transcribed into RNA, or only a portion of the oligonucleotides are transcribed into RNA. For example, all of the oligonucleotides may contain the same promoter; or only a subset of the oligonucleotides may contain the promoter. In some cases, the oligonucleotides comprise different promoters.

Polymerase Chain Reaction (PCR)

PCR reactions may be used at any step described herein. PCR reactions may be used, for example, to (i) perform bead-based synthesis of DNA constructs that incorporate promoters, primers, adaptors, and/or unique N-mer cell tags, (ii) perform bead-based synthesis of DNA constructs that incorporate promoters, primers, adaptors, and/or unique N-mer molecule tags, (iii) perform bead-based synthesis of DNA constructs that incorporate promoters, primers, adaptors, and/or both unique N-mer cell tags and/or unique N-mer molecule tags, (iv) perform general amplification of pooled cDNA libraries, or (v) to perform sequence-specific amplification of cDNA sequences that represent the target genes or oligonucleotide sequences of interest. In some preferred approaches, emulsion PCR using either the AmpliTaq or Phusion polymerase, single-stranded primer (e.g. Roche 454 primer A) attached to beads (e.g. Roche 454 beads), and a DNA construct comprising the 454 A and/or 454 B primer sequences, The T7 promoter, a partial Illumina adaptor sequence, an N-mer cell tag, a universal adapter sequence ending in GGG, and an optional restriction site sequence is used to synthesize double-stranded DNA on beads, which are then used to perform bead-based in vitro transcription (following treatment of the beads with a blunt-end restriction digest, if necessary to remove the restriction site) to produce RNA template switching oligos that incorporate the N-mer cell tag.

Although many of the examples disclosed herein describe bead-based synthesis of DNA constructs using emulsion PCR, the PCR synthesis and amplification reactions may also be performed in solution to synthesize said DNA constructs. Any of a number of known DNA polymerase systems (including the polymerase, suitable primers, necessary cofactors and buffers, and deoxyribonucleotide triphosphates) may be used under the appropriate set of reaction conditions (e.g., suitable melt temperatures, annealing temperatures, and elongation reaction temperatures) to perform the synthesis or amplification. Exemplary systems include the Phusion polymerase system, the Taq polymerase system, the AmpliTaq polymerase system, or any other suitable polymerase system. Preferentially, the polymerase chosen for use in PCR reactions used to synthesize the DNA constructs described above is one that does not add overhanging A bases at the 3' end of the construct, as this necessitates removal using T4 DNA polymerase or other suitable exonuclease.

In some cases, PCR reactions are used with an appropriate set of primers in a general fashion to synthesize and/or amplify all DNA template or cDNA library molecules. In other cases, PCR reactions are used with an appropriate set of primers in a selective fashion to specifically amplify those target gene sequences or target oligonucleotide sequences present in the cDNA library. In some cases, both general and specific PCR reactions are performed. The number of PCR reaction cycles utilized may vary from about 2 cycles to 40 cycles or more.

DNA Sequencing

DNA sequencing may be used to sequence the pooled and amplified cDNA library in order to identify: (i) the identity of the cell tag, (ii) the identity of the molecule tag, and/or (iii) the complete or partial sequence of the target genes or oligonucleotides of interest. DNA sequencing is performed using any of a number of commercially-available sequencing systems (i.e. reagents, kits, and instruments), for example the Illumina MiSeq, HiSeq, or NextSeq 500 systems; the Life Technologies SOLID sequencing system, the Pacific Biosciences SMRT sequencing system, or any of the other commercially-available or emerging sequencing technology platforms. The choice of adapter sequences incorporated into the design of the DNA or RNA constructs used for adding cell tags and/or molecule tags to the cDNA library is driven by the choice of sequencing system used.

In certain embodiments, the sequencing technique used in the methods of the provided invention generates at least 100 reads per run, at least 200 reads per run, at least 300 reads per run, at least 400 reads per run, at least 500 reads per run, at least 600 reads per run, at least 700 reads per run, at least 800 reads per run, at least 900 reads per run, at least 1000 reads per run, at least 5,000 reads per run, at least 10,000 reads per run, at least 50,000 reads per run, at least 100,000 reads per run, at least 500,000 reads per run, at least 1,000,000 reads per run, at least 2,000,000 reads per run, at least 3,000,000 reads per run, at least 4,000,000 reads per run at least 5000,000 reads per run, at least 6,000,000 reads per run at least 7,000,000 reads per run at least 8,000,000 reads per run, at least 9,000,000 reads per run, or at least 10,000,000 reads per run.

In some embodiments the number of sequencing reads per B cell sampled should be at least 2 times the number of B cells sampled, at least 3 times the number of B cells sampled, at least 5 times the number of B cells sampled, at least 6 times the number of B cells sampled, at least 7 times the number of B cells sampled, at least 8 times the number of B cells sampled, at least 9 times the number of B cells sampled, or at least at least 10 times the number of B cells The read depth allows for accurate coverage of B cells sampled, facilitates error correction, and ensures that the sequencing of the library has been saturated.

In some embodiments the number of sequencing reads per T-cell sampled should be at least 2 times the number of T-cells sampled, at least 3 times the number of T-cells sampled, at least 5 times the number of T-cells sampled, at least 6 times the number of T-cells sampled, at least 7 times the number of T-cells sampled, at least 8 times the number of T-cells sampled, at least 9 times the number of T-cells sampled, or at least at least 10 times the number of T-cells The read depth allows for accurate coverage of T-cells sampled, facilitates error correction, and ensures that the sequencing of the library has been saturated.

VI. Mechanisms for Partitioning and Merging

The methods and compositions provided in this disclosure may be implemented in partitions. These partitions may contain single cells for analysis of a sample at the single cell level. These partitions may contain tags or means for delivering tags. These partitions may comprise droplets, microwell arrays, microarrays, or any other suitable technology.

A. Droplets

In some cases, partitioning is performed with droplets. Droplets may comprise an aqueous medium (e.g. water, buffer solution, cell growth medium) surrounded by an immiscible oil phase (e.g. mineral oil, silicone oil, perfluorinated oil). Droplets may comprise an aqueous medium (e.g. water, buffer solution, cell growth medium) surrounded by air. Droplets may be located in a vial, tube, capillary, syringe, microfluidic channel, or on a surface (e.g. a piezoelectric surface for droplet actuation by surface acoustic waves). Droplets may be generated by any appropriate method, such as a microfluidic device (e.g., RainDance RainDrop system, microfluidic T-junction), bulk emulsification, or pipetting.

Droplets may additionally be formed with surfactants. Examples of surfactants include Triton X-100, SDS, ABIL EM90, Span80, monolein, oleic acid, Tween 20, Tween 80, Synperonic PEF, C12E8, n-Butanol, phospholipids, PF-octanol, PF-decanol, PF-TD OEG, PFPE-COOH, PFPE-COONH$_4$, PFPE-PEG, PFPE-DMP, and Pico-Surf.

Droplets may be sorted. For example, a sample containing cells may be partitioned into droplets containing cells (e.g., at most one cell) and droplets that contain no cells. Droplets containing zero cells may be sorted and discarded. Droplets may be sorted by any appropriate method, such as a microfluidic droplet sorting device or fluorescence-activated droplet sorting (FADS) system.

Droplets may be merged. For example, a droplet containing a cell or cell lysate may be merged with a droplet containing tags. Droplet merging may be conducted by any appropriate means, including passive droplet merging (e.g. at a microfluidic junction) and active droplet merging (e.g. electric, magnetic, thermal, or optical means).

The number of cells partitioned may be at least 10, at least 100, at least 1000, at least 10,000, or at least 100,000. Partitions may include at most one cell, at most two cells, at most three cells, at most four cells, at most five cells, or at most ten cells.

B. Microwell Arrays

In some cases, partitioning is performed with one or more microwell arrays. Microwell arrays may comprise plates, films, tapes, or other substrates comprising an array of microwells. The substrate may comprise plastic (e.g. polystyrene, polypropylene, polycarbonate, cyclo-olefin, Lucite), epoxy, photoresist (e.g. SU-8), PDMS, glass, metal, or any other suitable material. Microwell arrays may comprise at least 1, at least 6, at least 24, at least 96, at least 384, at least 1536, at least 3456, or at least 9600 wells. Sample may be distributed in the microwells by pipetting, liquid handlers, robotic fluid handlers, or any other appropriate method.

Microwell contents may be sorted. For example, a sample containing cells may be partitioned into microwells containing at most one cell, according to Poisson distribution statistics. Microwell contents containing zero cells may be chosen to be discarded. Microwell contents may be sorted by any appropriate method, such as fluorescence or optical detection. Microwell contents to be discarded may be removed from the microwells by pipetting, liquid handlers, robotic fluid handlers, or any other appropriate method.

Microwell contents may be merged. For example, the contents of a microwell with a cell or cell lysate may be merged with the contents of a microwell containing tags. Microwell content merging may be conducted by any appropriate method, including pipetting, liquid handling, robotic fluid handling, or physical alignment and contacting of multiple microwell plates.

The number of cells partitioned may be at least 10, at least 100, at least 1000, at least 10,000, or at least 100,000. Partitions may include at most one cell, at most two cells, at most three cells, at most four cells, at most five cells, or at most ten cells. In some cases, the microwells are designed to accommodate not more than one cell and/or not more than one bead. For example, the diameter of the microwells may be less than 10, 15, 20, 30, 35, 40, 45, 50, 55, 60, 65, 70, 75, 80, 85, 90, 95, 100, 105, 100, 110, 120, 130, 140, 150, 160, 170, 180, 190, 200, 250, or 300 um.

C. Microarrays with Dividers

In some cases, partitioning is performed with one or more microarray chips. Microarray chips may comprise chips, slides, or other substrates comprising an array of locations with bound material. The substrate may comprise glass, silicon, nylon, plastic, or any other suitable material. The material bound to the array locations may comprise DNA, RNA, proteins, peptides, antibodies, cells, chemicals, tissues, or carbohydrates.

Material bound to microarray locations may be further partitioned by inclusion of dividers or walls. A membrane or material layer comprising dividers or walls may be aligned and bonded to the microarray surface, partitioning each microarray location and providing a partitioned volume. The membrane may comprise PDMS, glass, silicon, plastic (e.g. PMMA), metal, or any other suitable material.

Subsequent to partitioning by divider, the contents of a microarray location may be detached from the substrate, or may be replicated, to produce unbound copies of the location contents. For example, a microarray location containing surface-bound DNA may be reacted to produce RNA molecules in free solution by in vitro transcription.

Microarray location volume contents may be merged. For example, the contents of a microarray location volume containing tags may be merged with a volume containing cells or cell lysate. Microarray location volume content merging may be conducted by any appropriate method, including pipetting, liquid handling, robotic fluid handling, or physical alignment and contacting with microwell plates or other partitioned microarrays.

VI. Digital Counting and Analysis

The high throughput sequencing provides a very large dataset.

High-throughput analysis can be achieved using one or more bioinformatics tools, such as ALLPATHS (a whole genome shotgun assembler that can generate high quality assemblies from short reads), Arachne (a tool for assembling genome sequences from whole genome shotgun reads, mostly in forward and reverse pairs obtained by sequencing cloned ends, BACCardl (a graphical tool for the validation of genomic assemblies, assisting genome finishing and intergenome comparison), CCRaVAT & QuTie (enables analysis of rare variants in large-scale case control and quantitative trait association studies), CNV-seq (a method to detect copy number variation using high throughput sequencing), Elvira (a set of tools/procedures for high throughput assembly of small genomes (e.g., viruses)), Glimmer (a system for finding genes in microbial DNA, especially the genomes of bacteria, archaea and viruses), gnumap (a program designed to accurately map sequence data obtained from next-generation sequencing machines), Goseq (an R library for performing Gene Ontology and other category based tests on RNA-seq data which corrects for selection bias), ICAtools (a set of programs useful for medium to large scale sequencing projects), LOCAS, a program for assembling short reads of second generation sequencing technology, Maq (builds assembly by mapping short reads to reference sequences, MEME (motif-based sequence analysis tools, NGSView (allows for visualization and manipulation of millions of sequences simultaneously on a desktop computer, through a graphical interface, OSLay (Optimal Syntenic Layout of Unfinished Assemblies), Perm (efficient mapping for short sequencing reads with periodic full sensitive spaced seeds, Projector (automatic contig mapping for gap closure purposes), Qpalma (an alignment tool targeted to align spliced reads produced by sequencing platforms such as Illumina, Solexa, or 454), RazerS (fast read mapping with sensitivity control), SHARCGS (SHort read Assembler based on Robust Contig extension for Genome Sequencing; a DNA assembly program designed for de novo assembly of 25-40 mer input fragments and deep sequence coverage), Tablet (next generation sequence assembly visualization), and Velvet (sequence assembler for very short reads).

A Non-limiting example of data analysis steps are summarized below:

Grouping reads with the same cellular and/or molecular tag: Initially sequences are matched based on identical cellular and or molecular tags.

Build a minimum spanning forest for each group: Cluster into sungroups (trees) if Hamming distance is greater than 5%.

For each subgroup (or tree), create a vector of sums of correct probabilities for each called base in each read.

Construct a consensus read from the base with the maximum sum in each position: Consensus reads are used for mutation analysis and diversity measurement.

VII. Information Systems

Figure 18:
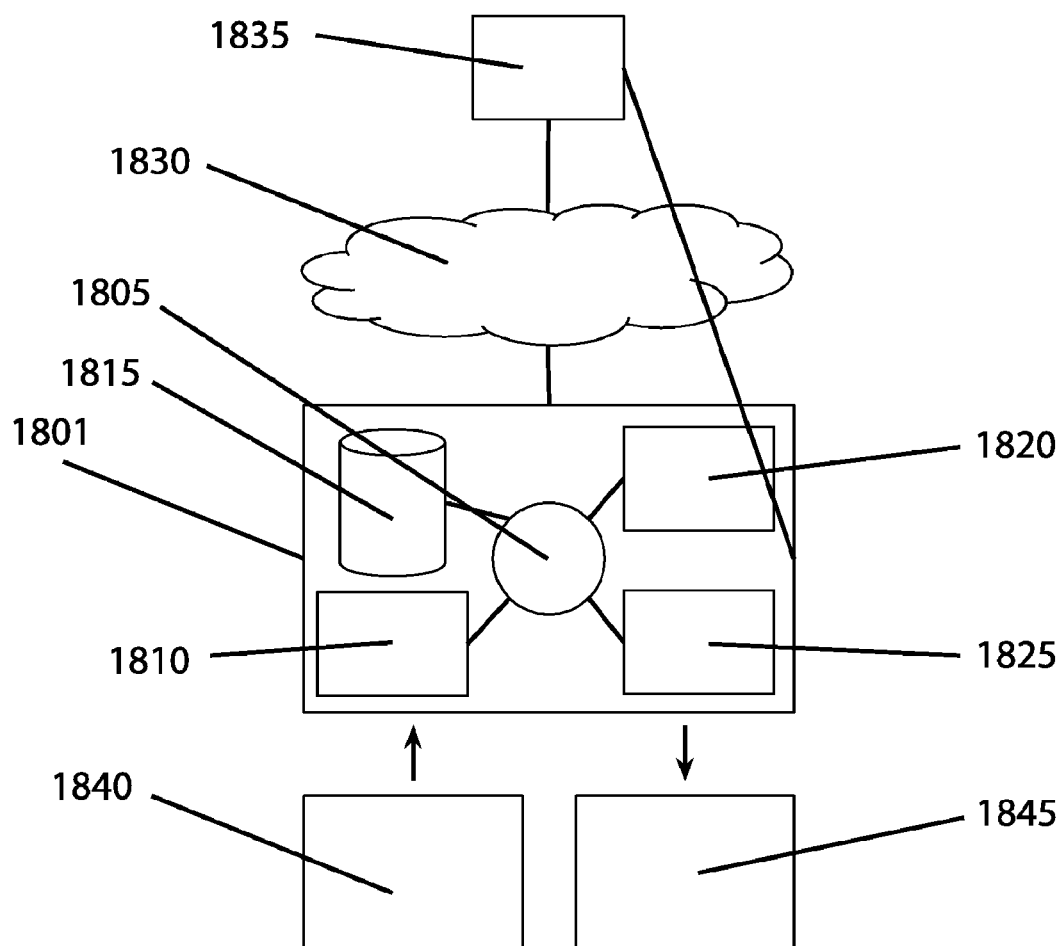
FIG. 18 depicts the use of information systems in analysis.

The methods provided herein may be processed on a server or a computer server (FIG. 18). The server [1801] includes a central processing unit (CPU, also "processor") [1805] which can be a single core processor, a multi core processor, or plurality of processors for parallel processing. A processor used as part of a control assembly may be a microprocessor. The server [1801] also includes memory

[1810] (e.g. random access memory, read-only memory, flash memory); electronic storage unit [1815] (e.g. hard disk); communications interface [1820] (e.g. network adaptor) for communicating with one or more other systems; and peripheral devices [1825] which may include cache, other memory, data storage, and/or electronic display adaptors. The memory [1810], storage unit [1815], interface [1820], and peripheral devices [1825] are in communication with the processor [1805] through a communications bus (solid lines), such as a motherboard. The storage unit [1815] can be a data storage unit for storing data. The server [1801] is operatively coupled to a computer network ("network") [1830] with the aid of the communications interface [1820]. A processor with the aid of additional hardware may also be operatively coupled to a network. The network [1830] can be the Internet, an intranet and/or an extranet, an intranet and/or extranet that is in communication with the Internet, a telecommunication or data network. The network [1830] in some cases, with the aid of the server [1801], can implement a peer-to-peer network, which may enable devices coupled to the server [1801] to behave as a client or a server. In general, the server may be capable of transmitting and receiving computer-readable instructions (e.g., device/system operation protocols or parameters) or data (e.g., sensor measurements, raw data obtained from detecting nucleic acids, analysis of raw data obtained from detecting nucleic acids, interpretation of raw data obtained from detecting nucleic acids, etc.) via electronic signals transported through the network [1830]. Moreover, a network may be used, for example, to transmit or receive data across an international border.

VIII. Applications

The invention finds use in the prevention, treatment, detection, diagnosis, prognosis, or research into any condition or symptom of any condition, including cancer, inflammatory diseases, autoimmune diseases, allergies and infections of an organism (i.e., bacterial, viral or fungal). The organism is preferably a human subject but can also be derived from non-human subjects, e.g., non-human mammals. Examples of non-human mammals include, but are not limited to, non-human primates (e.g., apes, monkeys, gorillas), rodents (e.g., mice, rats), cows, pigs, sheep, horses, dogs, cats, or rabbits.

Examples of cancer include prostrate, pancreas, colon, brain, lung, breast, bone, and skin cancers. Examples of inflammatory conditions include irritable bowel syndrome, ulcerative colitis, appendicitis, tonsilitis, dermatitis. Examples of atopic conditions include allergy, asthma, etc. Examples of autoimmune diseases include IDDM, RA, MS, SLE, Crohn's disease, Graves' disease, etc. Autoimmune diseases also include Celiac disease, and dermatitis herpetiformis. For example, determination of an immune response to cancer antigens, autoantigens, pathogenic antigens, vaccine antigens, and the like is of interest.

One specific application of the claimed methods is to assess the diversity of the immune repertoire of a subject.

VDJ lineage diversity: VDJ usage is enumerated by the number of observed lineages falling into each VJ, VDJ, VJC, or VDJC (e.g., VDJ) combination at a given read-depth.

VDJ and unique sequence abundance histograms: Histograms are plotted by binning VDJ and unique sequence abundances (the latter which is either clustered or has undergone lineage-analysis filtering and grouping) into log-spaced bins.

3D representation of VJ, VDJ, VJC, or VDJC (e.g., VDJ) usage: Repertoires are represented by applying V-, D-, J-, and/or C-segments to different axes on a three-dimensional plot. Using either abundance (generally read number, which can be bias-normalized) or observed lineage diversity, bubbles of varying sizes are used at each V/D/J/C coordinate to represent the total usage of that combination.

Mutation vs. sequence abundance plots: After undergoing lineage analysis, unique sequences are binned by read-number (or bias-normalized abundance) into log-spaced bins. For a given abundance-bin, the number of mutations per unique sequence is averaged, giving a mutation vs. abundance curve.

Correlative measures of V, D, J, C, VJ, VDJ, VJC, VDJC, antibody heavy chain, antibody light chain, CDR3, or T-cell receptor usage (Pearson, KL divergence): VJ, VDJ, VJC, or VDJC (e.g., VDJ) combinations are treated as vectors with indexed components v, weighted by either lineage-diversity or abundance for that VDJ combination. Pearson correlations and KL-divergences between each pair of individuals are then calculated over the indices.

The results of the analysis may be referred to herein as an immune repertoire analysis result, which may be represented as a dataset that includes sequence information, representation of V, D, J, C, VJ, VDJ, VJC, VDJC, antibody heavy chain, antibody light chain, CDR3, or T-cell receptor usage, representation for abundance of V, D, J, C, VJ, VDJ, VJC, VDJC, antibody heavy chain, antibody light chain, CDR3, or T-cell receptor and unique sequences; representation of mutation frequency, correlative measures of VJ V, D, J, C, VJ, VDJ, VJC, VDJC, antibody heavy chain, antibody light chain, CDR3, or T-cell receptor usage, etc. Such results may then be output or stored, e.g. in a database of repertoire analyses, and may be used in comparisons with test results, reference results, and the like.

After obtaining an immune repertoire analysis result from the sample being assayed, the repertoire can be compared with a reference or control repertoire to make a diagnosis, prognosis, analysis of drug effectiveness, or other desired analysis. A reference or control repertoire may be obtained by the methods of the invention, and will be selected to be relevant for the sample of interest. A test repertoire result can be compared to a single reference/control repertoire result to obtain information regarding the immune capability and/or history of the individual from which the sample was obtained. Alternately, the obtained repertoire result can be compared to two or more different reference/control repertoire results to obtain more in-depth information regarding the characteristics of the test sample. For example, the obtained repertoire result may be compared to a positive and negative reference repertoire result to obtain confirmed information regarding whether the phenotype of interest. In another example, two "test" repertoires can also be compared with each other. In some cases, a test repertoire is compared to a reference sample and the result is then compared with a result derived from a comparison between a second test repertoire and the same reference sample.

Determination or analysis of the difference values, i.e., the difference between two repertoires can be performed using any conventional methodology, where a variety of methodologies are known to those of skill in the array art, e.g., by comparing digital images of the repertoire output, by comparing databases of usage data, etc.

A statistical analysis step can then be performed to obtain the weighted contribution of the sequence prevalence, e.g. V, D, J, C, VJ, VDJ, VJC, VDJC, antibody heavy chain, antibody light chain, CDR3, or T-cell receptor usage, mutation analysis, etc. For example, nearest shrunken centroids analysis may be applied as described in Tibshirani et at. (2002) P.N.A.S. 99:6567-6572 to compute the centroid for each class, then compute the average squared distance between a given repertoire and each centroid, normalized by the within-class standard deviation.

A statistical analysis may comprise use of a statistical metric (e.g., an entropy metric, an ecology metric, a variation of abundance metric, a species richness metric, or a species heterogeneity metric.) in order to characterize diversity of a set of immunological receptors. Methods used to characterize ecological species diversity can also be used in the present invention. See, e.g., Peet, Annu Rev. Ecol. Syst. 5:285 (1974). A statistical metric may also be used to characterize variation of abundance or heterogeneity. An example of an approach to characterize heterogeneity is based on information theory, specifically the Shannon-Weaver entropy, which summarizes the frequency distribution in a single number. See, e.g., Peet, Annu Rev. Ecol. Syst. 5:285 (1974).

The classification can be probabilistically defined, where the cut-off may be empirically derived. In one embodiment of the invention, a probability of about 0.4 can be used to distinguish between individuals exposed and not-exposed to an antigen of interest, more usually a probability of about 0.5, and can utilize a probability of about 0.6 or higher. A "high" probability can be at least about 0.75, at least about 0.7, at least about 0.6, or at least about 0.5. A "low" probability may be not more than about 0.25, not more than 0.3, or not more than 0.4. In many embodiments, the above-obtained information is employed to predict whether a host, subject or patient should be treated with a therapy of interest and to optimize the dose therein.

In addition the methods described herein are of interest as a means of detecting the earliest changes along a disease pathway (e.g., a carcinogenesis pathway, inflammatory pathway, etc.), and/or to monitor the efficacy of various therapies and preventive interventions.

The methods disclosed herein can also be utilized to analyze the effects of agents on cells. For example, analysis of changes in gene expression following exposure to one or more test compounds can performed to analyze the effect(s) of the test compounds on an individual.

Agents to be analyzed for potential therapeutic value can be any compound, small molecule, protein, lipid, carbohydrate, nucleic acid or other agent appropriate for therapeutic use. Preferably tests are performed in vivo, e.g. using an animal model, to determine effects on the immune repertoire.

Agents of interest for screening include known and unknown compounds that encompass numerous chemical classes, primarily organic molecules, which may include organometallic molecules, genetic sequences, etc. An important aspect of the invention is to evaluate candidate drugs, including toxicity testing; and the like.

Test compounds include all of the classes of molecules described above, and can further comprise samples of unknown content. Of interest are complex mixtures of naturally occurring compounds derived from natural sources such as plants, fungi, bacteria, protists or animals. While many samples will comprise compounds in solution, solid samples that can be dissolved in a suitable solvent may also be assayed. Samples of interest include environmental samples, e.g., ground water, sea water, mining waste, etc., biological samples, e.g. lysates prepared from crops, tissue samples, etc.; manufacturing samples, e.g. time course during preparation of pharmaceuticals; as well as libraries of compounds prepared for analysis; and the like (e.g., compounds being assessed for potential therapeutic value, i.e., drug candidates).

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1—Preparing Beads with Cell Tags and Molecular Tags

Figure 10:
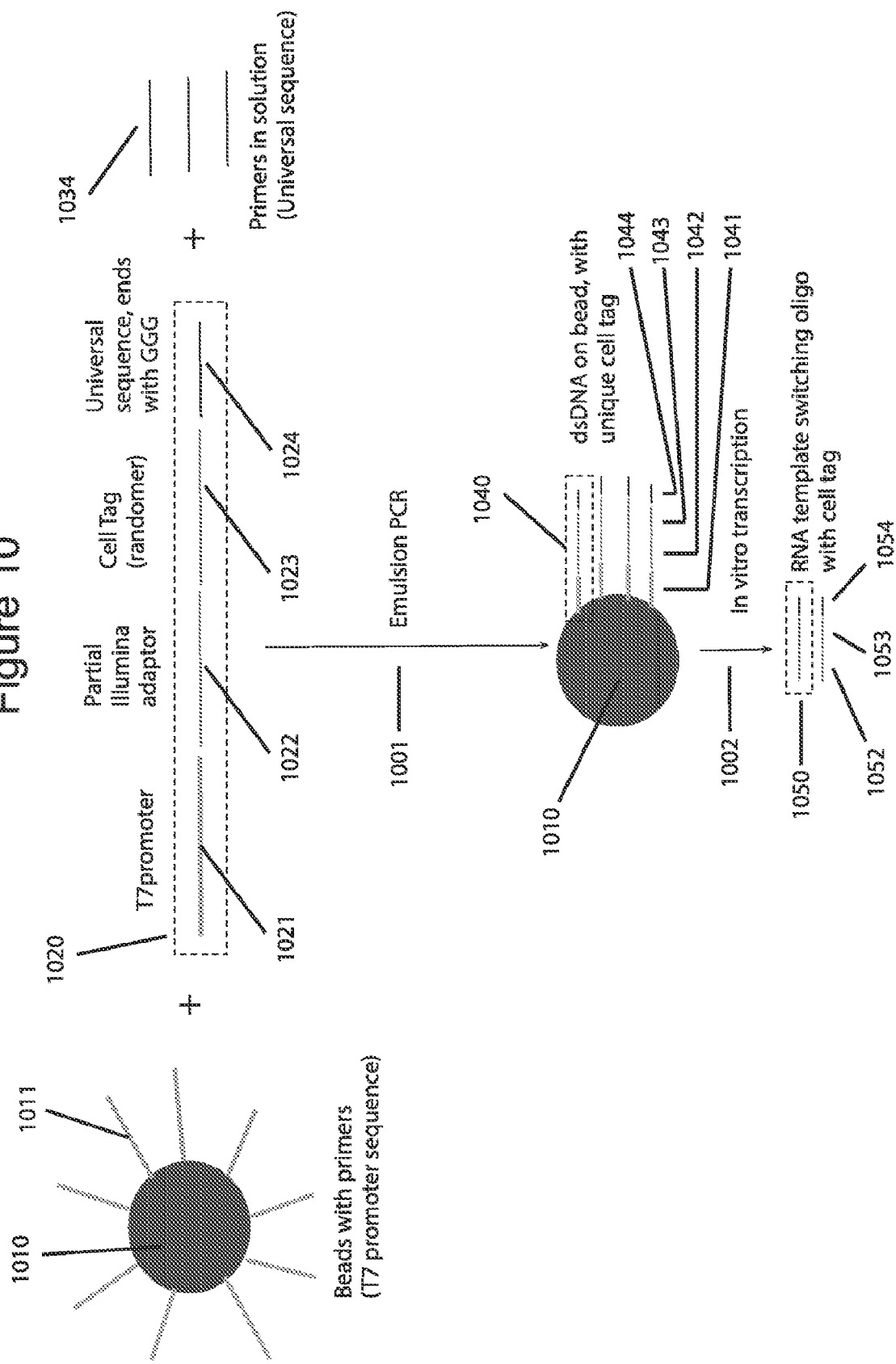
FIG. 10 depicts preparation of an oligonucleotide-conjugated bead and generation of a tag-bearing oligonucleotide from the bead.

Beads conjugated to dsDNA comprising cellular tags may be prepared as shown in FIG. 10. A bead with DNA bound to the surface is placed in solution with oligonucleotides, primers, enzymes, and other necessary reagents for performing PCR. In some cases the DNA [1011] bound to the bead [1010] comprises one region: a promoter region. The promoter region can be a T7 promoter. In some cases, the oligonucleotides [1020] in solution comprise four regions: a promoter region [1021], a partial sequencing adaptor [1022], a randomer cell tag [1023], and a universal sequence [1024]. The promoter region can be a T7 promoter. The partial sequencing adaptor can be a partial Illumina adaptor. The universal sequence can end with GGG. In some cases, the primers in the solution [1034] comprise a universal sequence. PCR is then conducted. In some cases, the PCR is emulsion PCR [1001]. The PCR reaction may result in additional sequences being added to the DNA bound to the bead. In some cases, the resulting DNA is double-stranded DNA. In some cases the dsDNA [1040] comprises six regions: a promoter region [1041], a partial sequencing adaptor region [1042], a randomer cell tag [1043], and a universal sequence [1044]. The promoter region can be a T7 promoter. The partial sequencing adaptor region can be a partial Illumina adapter. The universal sequence can end with GGG. In vitro transcription is then conducted [1002], producing RNA oligonucleotide products [1050]. In some cases, the oligonucleotide products comprise three regions: a partial sequencing adaptor region [1052], a randomer cell tag [1053], and a universal sequence [1054]. The partial sequencing adaptor region can be a partial Illumina adapter. The universal sequence can end with GGG.

Figure 11:
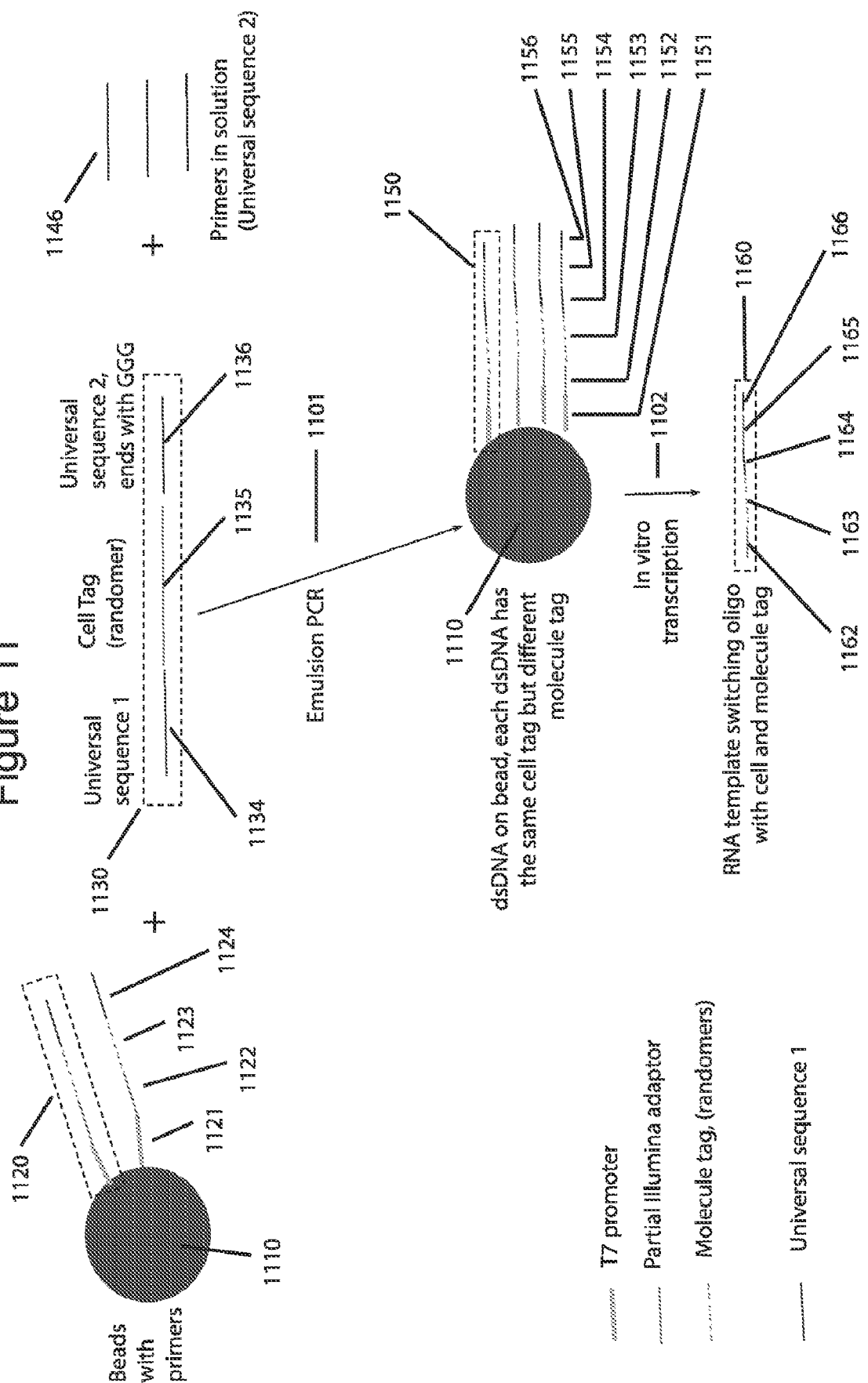
FIG. 11 depicts preparation of an oligonucleotide-conjugated bead and generation of a tag-bearing oligonucleotide from the bead.

Beads conjugated to dsDNA comprising cell tags and molecule tags may be prepared as depicted in FIG. 11. A bead with DNA bound to the surface is placed in solution with oligonucleotides, primers, enzymes, and other necessary reagents for performing PCR. In some cases the DNA [1120] bound to the bead [1110] comprises four regions: a promoter region [1121], a partial sequencing adaptor region [1122], a randomer molecule tag [1123] where each DNA molecule on the bead contains a different molecule tag sequence, and a first universal sequence [1124]. The promoter region can be a T7 promoter. The partial sequencing adaptor region can be a partial Illumina adapter. In some cases, the oligonucleotides [1130] in solution comprise three regions: a first universal sequence [1134], a randomer cell tag [1135], and a second universal sequence [1136]. The second universal sequence can end with GGG. In some cases, the primers in the solution [1146] comprise a second universal sequence. PCR is then conducted. In some cases, the PCR is emulsion PCR [1101]. As a result the DNA on the bead is extended, thereby incorporating additional sequences. The reaction can also be designed so that the resulting DNA conjugated to the bead is dsDNA. In some cases the dsDNA [1150] comprises six regions: a promoter region [1151], a partial sequencing adaptor region [1152], a randomer molecule tag [1153] where each dsDNA molecule on the bead contains a different molecule tag sequence, a first universal sequence [1154], a randomer cell tag [1155], and a second universal sequence [1156]. The promoter region can be a T7 promoter. The partial sequencing adaptor region can be a partial Illumina adapter. The second universal sequence can end with GGG. In vitro transcription is then conducted [1102], producing RNA oligonucleotide products [1160]. In some cases, the oligonucleotide products comprise five regions: a partial sequencing adaptor region [1162], a randomer molecule tag [1163] where oligonucleotide products from different dsDNA molecules on the bead contain different molecule tag sequences, a first universal sequence [1164], a randomer cell tag [1165], and a second universal sequence [1166]. The partial sequencing adaptor region can be a partial Illumina adapter. The second universal sequence can end with GGG.

Figure 12:
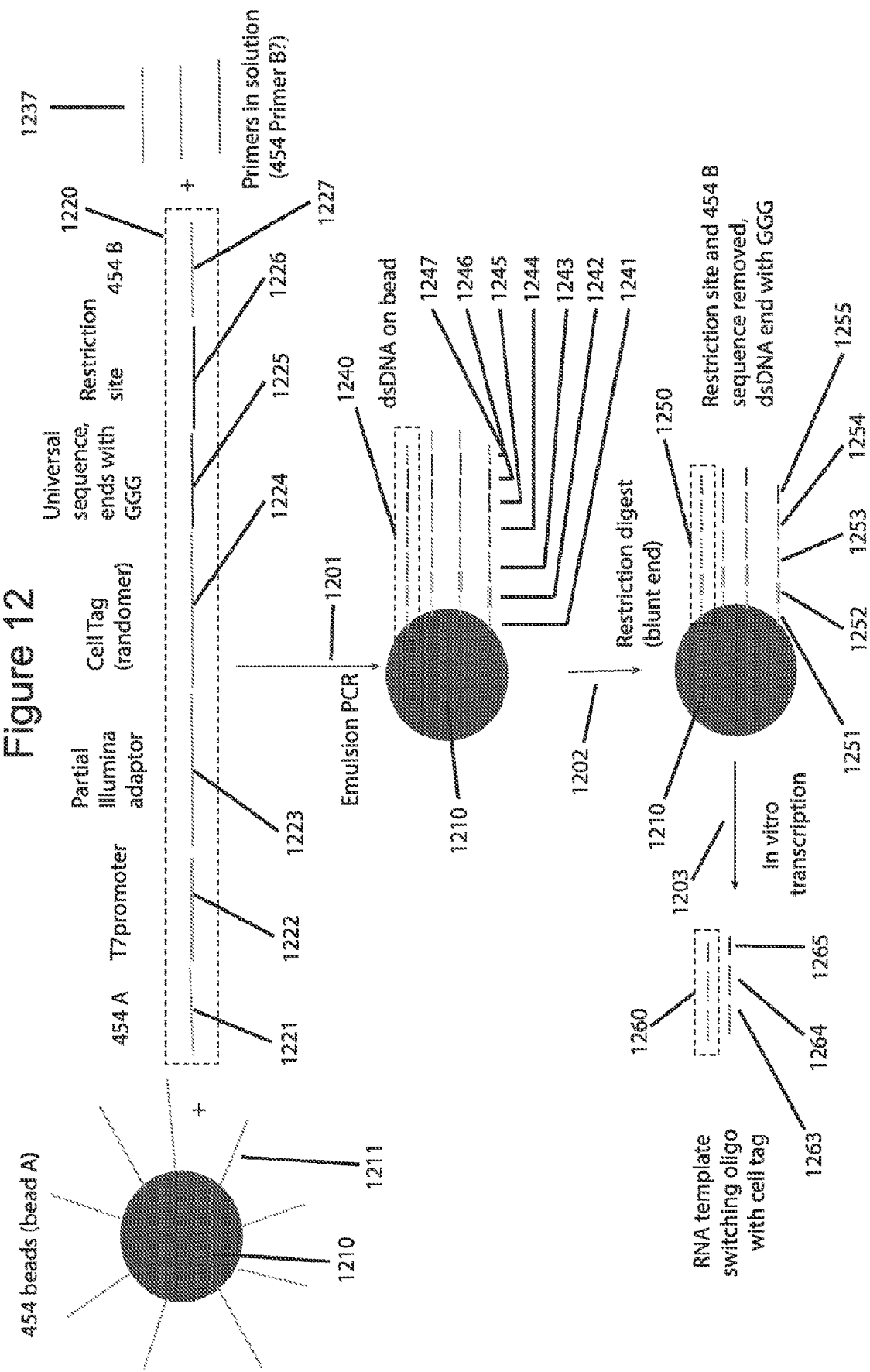
FIG. 12 depicts preparation of an oligonucleotide-conjugated bead and generation of a tag-bearing oligonucleotide from the bead.

FIG. 12 depicts another methods for preparing beads conjugated to dsDNA comprising a cell tag. In some cases the DNA [1211] bound to the bead [1210] comprises one region: an adaptor region [1211]. The adaptor region can be a 454 A adaptor. In some cases, the oligonucleotides [1220] in solution comprise seven regions: a first adaptor region [1221], a promoter region [1222], a partial sequencing adaptor region [1223], a randomer cell tag region [1224], a universal sequence [1225], a restriction site [1226], and a second adaptor region [1227]. The first and second adaptor regions can be 454 A and 454 B adaptors, respectively. The promoter region can be a T7 promoter. The partial sequencing adaptor region can be a partial Illumina adaptor. The universal sequence can end with GGG. In some cases, the primers in the solution [1237] comprise a second adaptor region sequence. The second adaptor region can be a 454 B adaptor. PCR is then conducted. In some cases, the PCR is emulsion PCR [1201]. This produces beads conjugated to dsDNA comprising multiple different regions. In some cases the dsDNA [1240] comprises seven regions: a first adaptor region [1241], a promoter region [1242], a partial sequencing adaptor region [1243], a randomer cell tag region [1244], a universal sequence [1245], a restriction site [1246], and a second adaptor region [1247]. The first and second adaptor regions can be 454 A and 454 B adaptors, respectively. The promoter region can be a T7 promoter. The partial sequencing adaptor region can be a partial Illumina adaptor. The universal sequence can end with GGG. A restriction digest may then be conducted. In some cases, the restriction digest is a blunt end restriction digest [1202]. This modifies the dsDNA bound to the bead surface. In some cases the surface-bound DNA then comprises five regions: an adaptor region [1251], a promoter region [1252], a partial sequencing adaptor region [1253], a randomer cell tag region [1254], and a universal sequence [1255]. The adaptor region can be a 454 A adaptor. The promoter region can be a T7 promoter. The partial sequencing adaptor region can be a partial Illumina adaptor. The universal sequence can end with GGG. In vitro transcription is then conducted [1203], producing RNA oligonucleotide products [1260]. In some cases, the oligonucleotide products comprise three regions: a partial sequencing adaptor region [1263], a randomer cell tag [1264], and a universal sequence [1265]. The partial sequencing adaptor region can be a partial Illumina adapter. The second universal sequence can end with GGG.

FIG. 13 depicts another method of producing beads conjugated to dsDNA comprising a cell tag. In some cases the dsDNA [1311] bound to the bead [1310] comprises one region: an adaptor region [1311]. The adaptor region can be a 454 A adaptor. In some cases, the oligonucleotides [1320] in solution comprise five regions: an adaptor region [1321], a promoter region [1322], a partial sequencing adaptor region [1323], a randomer cell tag region [1324], and a universal sequence [1325]. The adaptor region can be a 454 A adaptor. The promoter region can be a T7 promoter. The partial sequencing adaptor region can be a partial Illumina adaptor. The universal sequence can end with GGG. In some cases, the primers in the solution [1335] comprise a universal sequence. The universal sequence can end with GGG. PCR is then conducted. In some cases, the PCR is emulsion PCR [1301]. The PCR reaction may result in bead conjugated to dsDNA comprising a cell tag and the indicated regions. In some cases the dsDNA [1340] comprises five regions: an adaptor region [1341], a promoter region [1342], a partial sequencing adaptor region [1343], a randomer cell tag region [1344], and a universal sequence [1345]. The adaptor region can be a 454 A adaptor. The promoter region can be a T7 promoter. The partial sequencing adaptor region can be a partial Illumina adaptor. The universal sequence can end with GGG. The first and second adaptor regions can be 454 A and 454 B adaptors, respectively. The promoter region can be a T7 promoter. The partial sequencing adaptor region can be a partial Illumina adaptor. The universal sequence can end with GGG. In vitro transcription is then conducted [1302], producing RNA oligonucleotide products [1350]. In some cases, the oligonucleotide products comprise three regions: a partial sequencing adaptor region [1353], a randomer cell tag [1354], and a universal sequence [1355]. The partial sequencing adaptor region can be a partial Illumina adapter. The second universal sequence can end with GGG.

Example 2—High Throughput Single Cell RNA Tagging by Merging of Droplets

A first solution, containing a population of cells, is partitioned into a first series of droplets by a droplet generator (e.g. BioRad QX200 system, Dolomite Microfluidics systems, Micronit Microfluidics systems, water-in-oil microfluidic T-junction devices) using Poisson distribution statistics to ensure that each droplet contains 0 or 1 cells. A second solution, containing a population of beads from Example 1 as well as oligonucleotides, primers, enzymes, and other necessary reagents for PCR, in vitro transcription, and reverse transcription, is partitioned into a second series of droplets by a droplet generator using Poisson distribution statistics to ensure that each droplet contains 0 or 1 beads. Droplet generator systems are capable of generating tens of thousands of droplets, enabling high-throughput screening. Double-stranded DNA (dsDNA) is bound to the surface of the beads. The dsDNA may contain: (a) sequences for a promoter region (e.g., T7 promoter); (b) a sequencer adaptor region; (c) a randomer molecule tag region which is different for each DNA molecule on the bead; (d) a first universal sequence; (e) a second universal sequence ending with GGG; and/or (f) a randomer cell tag region which is the same for each DNA molecule on a particular bead. Droplets from the first series which contain 0 cells are discarded, and droplets from the second series which contain 0 beads are discarded. Discarding of droplets is performed by a droplet sorter (e.g. fluorescence-activated droplet sorting (FADS) system).

A set of reactions are carried out within the first series of droplets and the second series of droplets. The reactions may be conducted in parallel or sequentially. The first series of droplets is subjected to conditions which lyse the cells within the droplets. Reverse transcription is then conducted on the mRNA from the cell lysate, thereby producing cDNA transcripts within the droplets. The reverse transcription reaction may be performed using primers that are specific for certain regions of the mRNA; in some cases, the primers are general primers (e.g. as in QIAGEN QuantiTect Reverse Transcription Kit). (In some cases, the reverse transcription reaction occurs after a droplet from the first series of droplets is merged with another droplet, such as a droplet from the second series of droplets.) In the second series of droplets, the DNA molecules on the beads serve as templates for in vitro transcription reactions within the droplets which produce a set of mRNA transcripts from the DNA molecules encoding cellular and/or molecular tags. (In some cases, the in vitro transcription reaction occurs after a droplet from the second series is merged with another droplet, such as a droplet from the first series of droplets.)

Each single cell lysate-containing droplet is merged with one single bead transcript-containing droplet using a microfluidic device (e.g., RainDance RainDrop system, Dolomite Microfluidics systems). The GGG sequence in the mRNA tags then hybridizes to the overhanging CCC within the cellular cDNA. A reverse transcription reaction is then performed using the RNA tag as a template for an extension reaction. (e.g. FIG. 3, step [303]), resulting in tagging of the cellular cDNA with a DNA molecular/cellular tag.

Universal PCR is conducted on the pooled cDNA to further amplify the products. Target-specific PCR is conducted to target the genes of interest for sequencing. These target specific PCR products contain the genes of interest as well as the randomer cell and molecule tags and the sequencing adaptor sequence. These target specific PCR products are sequenced (e.g. by Illumina sequencing, where the sequencing adaptor sequences in the PCR products are Illumina tags). The information in the cell tag sequences is used to correlate specific genetic information with specific cells. The information in the molecule tag sequences is used to correlate specific genetic information with specific original mRNA molecules from each cell, allowing for correction of PCR amplification bias.

Example 3—Measurement of the Immune Response

A functional immune response (IR) assay is performed on sample comprising a population of cells, each expressing different immune receptors and comprising genes encoding immunoglobulin heavy chain or TCR beta, immunoglobulin light chain or TCR alpha, and various other genes related to immune function. The sample is partitioned into partitions containing immune cells. Each partitioned cell population may be lysed and its RNA may be extracted. The RNA from cell population is tagged with a molecule tag where the molecule tag is different for each molecule from a given cell by performing reverse transcription using an immunoglobulin or T-cell receptor and a template switching oligonucleotide comprising a molecule tag, and adapter sequence.

After tagging, the tagged RNA or its corresponding cDNA is pooled, amplified, and sequenced for analysis. The information from the expressed RNA may be used in combination with information from the molecule tags to determine the diversity of the immune response of a subject Example 4—Measurement of the Immune Response at the Single Cell Level A functional immune response (IR) assay is performed on sample comprising a population of single cells ([611], [612], [613], [614], [615], [616], [617], [618], [619]), each expressing different immune receptors [603] and comprising genes encoding immunoglobulin heavy chain or TCR beta [601], immunoglobulin light chain or TCR alpha [602], and various other genes related to immune function [604]. The sample is partitioned into partitions containing no more than one cell. Each partitioned cell may be lysed and its RNA may be extracted [605]. The RNA from each single cell is tagged with a cell tag where the cell tag is the same for every molecule from one given cell, and is also tagged with a molecule tag where the molecule tag is different for each molecule from a given cell.

After tagging, the tagged RNA or its corresponding cDNA ([621], [622], [623], [624], [625], [626], [627], [628], [629]) is pooled, amplified, and sequenced [606] for analysis. The information from the expressed RNA may be used in combination with information from the cell and/or molecule tags to categorize the cells into groups based on their immune function gene expression ([631], [632], [633], [634], [635], [636], [637], [638], [639]). This captures the information traditionally provided by multiple assays. For example, this immune response assay can provide information akin to that from an immune repertoire assay [710], flow cytometry [720], and a gene expression assay [730].

Example 5—Single Cell cDNA Tagging

FIG. 14 depicts incorporation of a cell tag onto the 5' end of a cDNA produced from cellular mRNA (corresponding to the 3' end of the mRNA) as well as incorporation of a molecular tag onto the 3' end of the cDNA (corresponding to the 5' end of the mRNA). The molecular tag is incorporated using RACE in this case and the cellular tag is added using a cDNA synthesis primer. The same procedure can be used to incorporate the cell tag onto the 3' end of the cDNA and the molecular tag onto the 5' end of the cDNA.

One cell or lysate from one cell is placed in a compartment. The cell may then be lysed in the compartment if it was not previously lysed. The lysate contains mRNA molecules [1410] containing an mRNA sequence and poly(A) tail [1414]. The compartment also contains oligodT molecules [1420]. In some cases, the oligodT molecules comprise five regions: an NVT region [1425], a TCA region [1426], a first universal sequence [1427], a randomer cell tag region [1428] where all oligodT molecules in a compartment have the same cell tag sequence, and a second universal sequence [1429]. The compartment also contains oligonucleotides [1430] which may comprise three regions: a universal sequence [1431], a randomer molecule tag [1432] where all oligonucleotides in the compartment have a different molecule tag sequence, and an overhang region [1433]. A reverse transcription reaction may be conducted using the oligodT region [1425] to primer the polyA tail present on the mRNA [1410]. The template switching oligonucleotide [1430] comprising the molecule tag may then be used as a template for the 5' RACE assay to add the molecule tag to the cDNA. This results in cDNA molecule products [1440]. In some cases, the cDNA molecules contain nine regions: a first universal sequence [1441], a randomer molecule tag [1432] where all original oligonucleotides in the compartment have a different molecule tag sequence, an overhang region [1433], an mRNA information sequence [1444] containing the information from the original mRNA molecules, an NVT region [1435], a TCA region [1436], a second universal sequence [1437], a randomer cell tag region [1438] where all cDNA molecules in a compartment have the same cell tag sequence, and a third universal sequence [1439].

The labeled cDNA products in a compartment are then pooled with labeled cDNA products from other compartments and amplified with universal PCR. The amplified cDNA products [1510] may comprise nine regions: a first universal sequence [1511], a randomer molecule tag [1512] where all original oligonucleotides from a given compartment have a different molecule tag sequence, an overhang region [1513], an mRNA information sequence [1514] containing the information from the original mRNA molecules, an NVT region [1515], a TCA region [1516], a second universal sequence [1517], a randomer cell tag region [1518] where all cDNA molecules from a given compartment (and therefore the products from those molecules) have the same cell tag sequence, and a third universal sequence [1519]. These PCR products are melted and the single stranded DNA (ssDNA) is circularized with enzymes. The circularization product cDNA molecules may comprise nine regions: a first universal sequence [1521], a randomer molecule tag [1522] where all original oligonucleotides from a given compartment have a different molecule tag sequence, an overhang region [1523], an mRNA information sequence [1524] containing the information from the original mRNA molecules, an NVT region [1525], a TCA region [1526], a second universal sequence [1527], a randomer cell tag region [1528] where all cDNA molecules from a given compartment (and therefore the products from those molecules) have the same cell tag sequence, and a third universal sequence [1529]. The circularization allows reordering of the regions to group together regions of interest for sequencing. Target specific PCR is conducted to amplify regions containing genes of interest as well as cell and molecular tags, which may then be sequenced and the information processed. The target specific PCR products may comprise seven regions: a first universal sequence [1531], a randomer molecule tag [1532] where all original oligonucleotides from a given compartment have a different molecule tag sequence, an overhang region [1533], an mRNA information sequence [1534] containing the information from the original mRNA molecules, a second universal sequence [1537], a randomer cell tag region [1538] where all cDNA molecules from a given compartment (and therefore the products from those molecules) have the same cell tag sequence, and a third universal sequence [1539].

Example 6—Single Cell cDNA Tagging Using a Microwell Array

The single cell cDNA tagging described in Example 4 may be conducted using the wells on a first microwell array plate as the compartments [1610], as depicted in FIG. 16. The oligodT molecules may be coupled to beads ([1611], [1612], [1613], [1614], [1615], [1616]) which are deposited with one bead per well. The microwell array plate may be designed to permit only one bead per well. For example, the wells may be no more than 100 micron in diameter. Master cDNA mix comprises the necessary reagents and enzymes, including the oligonucleotides with randomer molecule tags, for the generation of the labeled cDNA products described in Example 4. This master cDNA mix is also deposited in the wells. Random template-switching oligonucleotides may also be deposited into the wells. The wells may also optionally contain a lysis reagent. A second microwell array plate [1620] is loaded with cells ([1621], [1622], [1623], [1624], [1625], [1626]), with no more than one cell per well. The microwell array plate may be designed to permit only one cell per well. For example, the wells may be no more than 30 micron in diameter. The cells may be in PBS solution. The two microwell array plates are aligned to bring individual wells on the first plate in contact with individual wells on the second plate [1601]. The wells may be placed in an incubator at 42° C. Contact between the cell in one well and the cDNA mix in one other well causes lysis of the cell [1602]. After lysis, the beads may be collected and universal PCR may be conducted on the beads. In some instances, the compartments formed by the matched microwells are used as the compartments for the process described in Example 4.

Example 7—Single Cell cDNA Tagging Using a Microarray

The single cell cDNA tagging described in Example 4 may be conducted using the spots on a microarray, partitioned from each other, as the compartments [1640]. The oligodT molecules may be bound to individual spots on the array ([1641], [1642], [1643], [1644], [1645], [1646]) which are then partitioned from each other to form compartments. In some cases, the partitioning is achieved by aligning a PDMS membrane with wall or chamber features onto the array surface. Master cDNA mix comprises the necessary reagents and enzymes, including the oligonucleotides with randomer molecule tags, for the generation of the labeled cDNA products described in Example 4. This master cDNA mix is deposited hi the chambers. A microwell array plate [1650] is loaded with cells ([1651], [1652], [1653], [1654], [1655], [1656]), with no more than one cell per well. The cells may be in PBS solution. The microwell array plate and the microarray are aligned to bring individual wells on the microwell array plate in contact with individual chambers on the second plate [1601]. Contact between the cell in one well and the cDNA mix in one other well causes lysis of the cell [1603]. The compartments formed by the matched microwells and microarray chambers are then used as the compartments for the process described in Example 4.

What is claimed is:

1. A method of tagging target oligonucleotides comprising:
performing an in vitro transcription reaction on DNA molecules partitioned within a plurality of separate compartments, wherein each DNA molecule comprises an RNA polymerase promoter region, a randomer tag region, and a hybridization region capable of hybridizing to one or more target oligonucleotides, thereby obtaining compartments comprising RNA comprising the RNA polymerase promoter region, the randomer tag region and the hybridization region;
merging the interior of the compartments comprising RNA with the interior of a set of compartments comprising target oligonucleotides, wherein prior to the merging, the compartments comprising target oligonucleotides are physically separate from the compartments comprising RNA;
hybridizing the RNA to the target oligonucleotides; and
performing a reaction to attach a sequence corresponding to the RNA to the target oligonucleotides, thereby tagging the target oligonucleotides.

2. The method of claim 1, wherein the DNA is double stranded.

3. The method of claim 1, wherein the compartments are droplets within an oil-and-water emulsion.

4. The method of claim 1, wherein the randomer tag region comprises a random molecule tag such that each DNA molecule within a compartment comprises a different molecule tag, a cell tag such that the DNA molecules in each compartment includes a cell tag unique to the compartment, or a combination thereof.

5. The method of claim 1, wherein the target oligonucleotides are DNA.

6. The method of claim 4, wherein the randomer tag region comprises the random molecule tag and the cell tag.

7. The method of wherein the target oligonucleotides are obtained by lysing one or more cells within individual compartments of the set of compartments to liberate cellular oligonucleotides, wherein the cellular oligonucleotides are the target oligonucleotides.

8. The method of claim 1, wherein the target oligonucleotides are cellular oligonucleotides.

9. The method of claim 8, wherein the cellular oligonucleotides are cellular mRNA.

10. The method of claim 9, further comprising conducting a reverse transcription on the cellular mRNA to generate cellular cDNA.

11. The method of claim 10, wherein the target oligonucleotides are the cellular cDNA.

12. The method of claim 1, wherein the reaction is a Rapid Amplification of cDNA Ends (RACE) reaction.

13. The method of claim 10, wherein the reverse transcription reaction is performed with a primer specific for a region of the genome.

14. The method of claim 1, wherein the DNA is conjugated to a solid support.

15. The method of claim 14, wherein the solid support is a bead.

16. The method of claim 10, wherein the reverse transcription reaction is conducted within the set of compartments prior to the merging step.

17. The method of claim 10, wherein the reverse transcription reaction is conducted within the merged compartments.

18. The method of claim 13, wherein the region of the genome is an immunoglobulin gene or a T-cell receptor gene.

19. The method of claim 1, wherein the target oligonucleotides are cDNA generated from cellular mRNA.

20. The method of claim 1, wherein the hybridization region of the RNA comprises a homopolymeric tail.

21. The method of claim 19, wherein cDNA comprises overhanging C bases generated via the terminal transferase activity of a reverse transcriptase enzyme.

22. The method of claim 21, wherein the hybridization region of the RNA comprises a homopolymeric tail.

23. The method of claim 22, wherein the homopolymeric tail comprises a series of G bases.

24. The method of claim 23, wherein the hybridizing comprises hybridizing the series of G bases to the overhanging C bases.

25. The method of claim 1, wherein the RNA polymerase promoter sequence is the T7 RNA polymerase promoter sequence.

26. The method of claim 1, wherein the RNA polymerase promoter sequence is the T3 RNA polymerase promoter sequence.

27. The method of claim 4, wherein the random molecule tag is from 4 bases to 14 bases long.

28. The method of claim 4, wherein the cell tag is from 4 bases to 14 bases long.

* * * * *